(12) United States Patent
Page et al.

(10) Patent No.: US 9,394,306 B2
(45) Date of Patent: Jul. 19, 2016

(54) PYRAZOLINE DIONE DERIVATIVES AS NADPH OXIDASE INHIBITORS

(75) Inventors: Patrick Page, Saint-Julien-en-Genevois (FR); Francesca Gaggini, Geneva (CH); Benoît Laleu, Collonges-sous-Saleve (FR)

(73) Assignee: GENKYOTEX SA, Plan-les-Ouates (CH)

( * ) Notice: Subject to any disclaimer, the term of this patent is extended or adjusted under 35 U.S.C. 154(b) by 251 days.

(21) Appl. No.: 13/394,904

(22) PCT Filed: Sep. 27, 2010

(86) PCT No.: PCT/IB2010/054329
§ 371 (c)(1),
(2), (4) Date: Mar. 8, 2012

(87) PCT Pub. No.: WO2011/036651
PCT Pub. Date: Mar. 31, 2011

(65) Prior Publication Data
US 2012/0172352 A1  Jul. 5, 2012

(30) Foreign Application Priority Data

Sep. 28, 2009 (EP) ..................................... 09171466

(51) Int. Cl.
*A61K 31/551* (2006.01)
*C07D 471/14* (2006.01)
*C07D 498/14* (2006.01)
*C07D 513/14* (2006.01)

(52) U.S. Cl.
CPC ............ *C07D 471/14* (2013.01); *C07D 498/14* (2013.01); *C07D 513/14* (2013.01)

(58) Field of Classification Search
CPC ........................... A61K 31/551; C07D 471/14
USPC .......................................... 514/220; 540/559
See application file for complete search history.

(56) References Cited

U.S. PATENT DOCUMENTS

| | | | |
|---|---|---|---|
| 3,931,407 A | 1/1976 | Allen et al. | |
| 4,909,827 A | 3/1990 | Gehring et al. | |
| 5,869,516 A | 2/1999 | Arlt et al. | |
| 6,107,306 A | 8/2000 | Carpino et al. | |
| 6,624,309 B1 | 9/2003 | Lloyd et al. | |
| 8,288,432 B2 | 10/2012 | Page et al. | |
| 8,389,518 B2 | 3/2013 | Page et al. | |
| 8,404,742 B2 | 3/2013 | Wierzbicki et al. | |
| 8,455,485 B2 | 6/2013 | Page et al. | |
| 8,455,486 B2 | 6/2013 | Page et al. | |
| 8,481,562 B2 | 7/2013 | Page et al. | |
| 8,748,456 B2 | 6/2014 | Page et al. | |
| 8,865,758 B2 | 10/2014 | Page et al. | |
| 2007/0014739 A1 | 1/2007 | Eldridge et al. | |
| 2007/0037883 A1 | 2/2007 | Dusting et al. | |
| 2007/0082910 A1 | 4/2007 | Yamamoto et al. | |
| 2008/0176934 A1 | 7/2008 | Verbeuren et al. | |
| 2009/0099179 A1 | 4/2009 | Klein et al. | |
| 2010/0048560 A1 | 2/2010 | Page et al. | |
| 2010/0120749 A1 | 5/2010 | Page et al. | |
| 2011/0172266 A1 | 7/2011 | Page et al. | |
| 2011/0178081 A1 | 7/2011 | Page et al. | |
| 2011/0178082 A1 | 7/2011 | Page et al. | |
| 2011/0269757 A1 | 11/2011 | Page et al. | |
| 2012/0316163 A1 | 12/2012 | Page et al. | |
| 2012/0316380 A1 | 12/2012 | Page et al. | |
| 2013/0123256 A1 | 5/2013 | Page et al. | |
| 2013/0143879 A1 | 6/2013 | Page et al. | |
| 2013/0158027 A1 | 6/2013 | Page et al. | |
| 2013/0296362 A1 | 11/2013 | Page et al. | |

FOREIGN PATENT DOCUMENTS

| | | |
|---|---|---|
| DE | 102005048897 | 10/2005 |
| EP | 0274642 A | 7/1988 |
| EP | 1175900 | 1/2002 |
| EP | 1396493 | 3/2004 |
| EP | 1505068 | 2/2005 |
| EP | 2002835 A | 12/2008 |
| WO | WO 97/19679 | 6/1997 |
| WO | WO 02/088122 | 11/2002 |
| WO | WO 2004/005267 | 1/2004 |
| WO | WO 2005/080378 | 9/2005 |
| WO | WO 2006/041874 | 4/2006 |
| WO | WO 2006/094187 | 9/2006 |
| WO | WO 2008/113856 | 9/2008 |
| WO | WO 2008/116926 | 10/2008 |
| WO | WO 2009/072643 | 6/2009 |
| WO | WO 2010/035217 | 4/2010 |
| WO | WO 2010/035219 | 4/2010 |
| WO | WO 2010/035220 | 4/2010 |
| WO | WO 2010/035221 | 4/2010 |

(Continued)

OTHER PUBLICATIONS

Altenhofer et al., NOX Toolbox: Validating the Role of NADPH Oxidases in Physiology and Disease, Cell. Mol. Life Sci., vol. 69, pp. 2327-2343, 2012.*

Fujita, M. et al. "Pyrroloquinolones and pyrazoloquinolones as potential antibacterial agents. Synthesis and antibacterial activity" *European Journal of Medicinal Chemistry*, 1996, pp. 981-988, vol. 31.

Cai, H. et al. "The vascular NAD(P)H oxidases as therapeutic targets in cardiovascular diseases" *TRENDS in Pharmacological Sciences*, Sep. 2003, pp. 471-478, vol. 24, No. 9.

(Continued)

*Primary Examiner* — Brenda Coleman
(74) *Attorney, Agent, or Firm* — Saliwanchik, Lloyd & Eisenschenk

(57) ABSTRACT

The present invention is related to pyrazoline dione derivatives of Formula (I), pharmaceutical composition thereof and to their use for the treatment and/or prophylaxis of disorders or conditions related to Nicotinamide adenine dinucleotide phosphate oxidase (NADPH Oxidase).

22 Claims, No Drawings

(56) References Cited

FOREIGN PATENT DOCUMENTS

| WO | WO 2011/101804 | 8/2011 |
| WO | WO 2011/101805 | 8/2011 |

OTHER PUBLICATIONS

Thabut, G. et al. "Tumor Necrosis Factor-α Increases Airway Smooth Muscle Oxidants Production through a NADPH Oxidase-like System to Enhance Myosin Light Chain Phosphorylation and Contractility" *The Journal of Biological Chemistry*, Jun. 21, 2002, pp. 22814-22821, vol. 277, No. 25.

Djordjeivc, T. et al. "Human Urotensin II Is a Novel Activator of NADPH Oxidase in Human Pulmonary Artery Smooth Muscle Cells" *Arteriosclerosis, Thrombosis, and Vascular Biology*, 2005, pp. 519-525, vol. 25.

Yang, S. et al. "Characterization of Interferon Gamma Receptors on Osteoclasts: Effect of Interferon Gamma on Osteoclastic Superoxide Generation" *Journal of Cellular Biochemistry*, 2002, pp. 645-654, vol. 84.

Ellis, E. et al. "Increased $H_2O_2$, Vascular Endothelial Growth Factor and Receptors in the Retina of the BBZ/WOR Diabetic Rat" *Free Radical Biology & Medicine*, 2000, pp. 91-101, vol. 28, No. 1.

Pillarsetti, S. et al. "Role of oxidative stress and inflammation in the origin of Type 2 diabetes—a paradigm shift" *Expert Opinion on Therapeutic Targets*, 2004, pp. 401-408, vol. 8, No. 5.

Shi, Y. et al. "Increased NAD(P)H Oxidase and Reactive Oxygen Species in Coronary Arteries After Balloon Injury" *Arteriosclerosis, Thrombosis, and Vascular Biology*, 2001, pp. 739-745, vol. 21.

Brigham, K. L. "Role of Free Radicals in Lung Injury" *Chest*, Jun. 1986, pp. 859-863, vol. 89, No. 6.

Nunomura, A. et al. "Oxidative Damage Is the Earliest Event in Alzheimer Disease" *Journal of Neuropathology and Experimental Neurology*, Aug. 2001, pp. 759-767, vol. 60, No. 8.

Girouard, H. et al. "Neurovascular coupling in the normal brain and in hypertension, stroke, and Alzheimer disease" *Journal of Applied Physiology*, 2006, pp. 328-335, vol. 100.

Vernet, P. et al. "Analysis of Reactive Oxygen Species Generating Systems in Rat Epididymal and Spermatozoa" *Biology of Reproduction*, 2001, pp. 1102-1113, vol. 65.

Gaggini, F. et al. "Design, synthesis and biological activity of original pyrazolo-pyrido-diazepine, -pyrazine and -oxazine dione derivatives as novel dual Nox4/Nox1 inhibitors" *Bioorganic & Medicinal Chemistry*, 2011, pp. 6989-6999, vol. 19.

Liu, J. Q. et al. "Extracellular superoxide enhances 5-HT-induced murine pulmonary artery vasoconstriction" *American Journal of Physiology Lung Cellular and Molecular Physiology*, 2004, pp. L111-L118, vol. 287.

Written Opinion in International Application No. PCT/IB2010/054329, Mar. 1, 2011, pp. 1-8.

Hua, C. et al. "The vascular NAD(P)H oxidases as therapeutic targets in cardiovascular diseases" *TRENDS in Pharmacological Sciences*, Sep. 2003, pp. 471-478, vol. 24, No. 9.

Saxena, U. et al. "New approaches for treatment of diabetic nephropathy: the endothelium as a target for drug discovery" *Expert Opinion Ther. Targets*, 2001, pp. 539-545, vol. 5, No. 5.

Bedard, K. et al. "The NOX Family of ROS-Generating NADPH Oxidases: Physiology and Pathophysiology" *Physiological Reviews*, Jan. 2007, pp. 245-313, vol. 87.

Ferrara, N. et al. "Angiogenesis as a therapeutic target" *Nature*, Dec. 15, 2005, pp. 967-974, vol. 438.

Folkman, J. "Angiogenesis" *Annu. Rev. Med.*, 2006, pp. 1-18, vol. 57.

Griendling, K. K. et al. "NAD(P)H Oxidase: Role in Cardiovascular Biology and Disease" *Circulation Research*, 2000, pp. 494-501, vol. 86.

Ray, R. et al. "NADPH oxidase and endothelial cell function" *Clinical Science*, 2005, pp. 217-226, vol. 109.

Wu, D. et al. "NADPH oxidase mediates oxidative stress in the 1-methyl-4-phenyl-1,2,3,6-tetrahydropyridine model of Parkinson's disease" *PNAS*, May 13, 2003, pp. 6145-6150, vol. 100. No. 10.

Garrido-Urbani, S. et al. "Targeting Vascular NADPH Oxidase 1 Blocks Tumor Angiogenesis through a PPARα Mediated Mechanism" *PLoS One*, Feb. 2011, pp. 1-13, vol. 6, Issue 2.

Chang, G. et al. "Specific Inhibition of NADP(H) Oxidase (NOX) Abrogates the Tumorigenic Phenotype of Renal Cancer Cells" Poster at Annual Meeting of the Society of Basic Urology, Nov. 2009, New Orleans, USA, p. 1.

Jain, V. K. et al. "NADPH Oxidase and Myeloperoxidase Activity in Psoriasis Leukocytes" *The Journal of Dermatology*, 1985, pp. 425-428, vol. 12.

Baker, M. A. et al. "Reactive oxygen species in spermatozoa: methods for monitoring and significance for the origins of genetic disease and infertility" *Reproductive Biology and Endorcinology*, 2005, pp. 1-9, vol. 3, No. 67.

Chen, P. et al. "Role of NADPH oxidase and ANG II in diabetes-induced retinal leukostasis" *Am. J. Physiol. Reul. Integr. Comp. Physiol.*, 2007, pp. R1619-R1629, vol. 293.

Cucoranu, I. et al. "NAD(P)H Oxidase 4 Mediates Transforming Growth Factor-b1-Induced Differentiation of Cardiac Fibroblasts Into Myofibroblasts" *Circulation Research*, 2005, pp. 900-907, vol. 97.

El Benna, J. et al. "NADPH Oxidase Priming and p47phox Phosphorylation in Neutrophils from Synovial Fluid of Patients with Rheumatoid Arthritis and Spondylarthropathy" *Inflammation*, Dec. 2002, pp. 273-278, vol. 26, No. 6.

Ellis E. A. et al. "Time Course of NADH Oxidase, Inducible Nitric Oxide Synthase and Peroxynitrite in Diabetic Retinopathy in the BBZ/WOR Rat" *Nitric Oxide: Biology and Chemistry*, 2002 pp. 295-304, vol. 6, No. 3.

Fukuyama, M. et al. "Overexpression of a novel superoxide-producing enzyme, NADPH oxidase 1, in adenoma and well differentiated adenocarcinoma of the human colon" *Cancer Letters*, 2005, pp. 97-104, vol. 221.

Gavazzi, G. et al. "NOX1 Deficiency Protects from Aortic Dissection in Response to Angiotensin II" *Hypertension*, 2007, pp. 189-196, vol. 50.

Gukovskaya, A. S. et al. "Neutrophils and NADPH Oxidase Mediate Intrapancreatic Trypsin Activation in Murine Experimental Acute Pancreatitis" *Gastroenterology*, 2002, pp. 974-984, vol. 122.

Hausmann, M. et al. "Subtractive screening reveals up-regulation of NADPH oxidase expression in Crohn's disease intestinal macrophages" *Clin. Exp. Immunol.*, 2001, pp. 48-55, vol. 125.

Hoidal, J. R. et al. "The Role of Endogenous NADPH Oxidases in Airway and Pulmonary Vascular Smooth Muscle Function" *Antioxidants & Redox Signaling*, 2003, pp. 751-758, vol. 5.

Inoguchi, T. et al. "NAD(P)H Oxidase Activation: A Potential Target Mechanism for Diabetic Vascular Complications, Progressive β-Cell Dysfunction and Metabolic Syndrome" *Current Drug Targets*, 2005, pp. 495-501, vol. 6.

Jin, L. et al. "NADPH oxidase: recent evidence for its role in erectile dysfunction" *Asian J. Androl.*, Jan. 2008, pp. 6-13, vol. 10.

Kawai, Y. et al. "Relationship of Intracellular Calcium and Oxygen Radicals to Cisplatin-Related Renal Cell Injury" *J. Pharmacot Sci.*, 2006, pp. 65-72, vol. 100.

Klees, R. F. et al. "Apocynin Derivatives Interrupt Intracellular Signaling Resulting in Decreased Migration in Breast Cancer Cells" *Journal of Biomedicine and Biotechnology*, 2006, pp. 1-10, vol. 2006.

Krijnen, P. A. et al. "Increased Nox2 expression in human cardiomyocytes after acute myocardial infarction" *J. Clin. Pathol.*, 2003, pp. 194-199, vol. 56.

Lanone S. et al. "Bilirubin decreases NOS2 expression via inhibition of NAD(P)H oxidase: implications for protection against endotoxic shock in rats" *The FASEB Journal*, 2005, pp. 1-26.

Lee, N. K. et al. "A crucial role for reactive oxygen species in RANKL-induced osteoclast differentiation" *Blood*, 2005, pp. 852-859, vol. 106.

Liu, Y. et al. "Suppression of Microglial Inflammatory Activity by Myelin Phagocytosis: Role of p47-PHOX-Mediated Generation of Reactive Oxygen Species" *The Journal of Neuroscience*, Dec. 13, 2006, pp. 12904-12913, vol. 26, No. 50.

(56) References Cited

OTHER PUBLICATIONS

Nibali, L. et al. "NADPH oxidase (CYBA) and FcγR polymorphisms as risk factors for aggressive periodontitis" *J. Clin. Periodontol*, 2006, pp. 529-539, vol. 33.

Patel, C. et al. "Prolonged Reactive Oxygen Species Generation and Nuclear Factor-κB Activation after a High-Fat, High-Carbohydrate Meal in the Obese" *The Journal of Clinical Endocrinology & Metabolism*, 2007, pp. 4476-4479, vol. 92, No. 111.

Patel, M. et al. "Activation of NAPDH oxidase and extracellular superoxide production in seizure-induced hippocampal damage" *Journal of Neurochemistry*, 2005, pp. 123-131, vol. 92.

Hougee, S. et al. "Oral administration of the NADPH-oxidase inhibitor apocynin partially restores diminished cartilage proteoglycan synthesis and reduces inflammation in mice" *European Journal of Pharmacology*, 2006, pp. 264-269, vol. 531.

Qian, L. et al. "Sinomenine, a natural dextrorotatory morphinan analog, is anti-inflammatory and neuroprotective through inhibition of microglial NADPH oxidase" *Journal of Neuroinflammation*, 2007, pp. 1-14, vol. 4, No. 23.

Ritsick, D. R. et al. "Spring brings breezes, wheezes, and pollen oxidases" *The Journal of Clinical Investigation*, Aug. 2005, vol. 115, No. 8.

Sato, K. et al. "In vivo lipid-derived free radical formation by NADPH oxidase in acute lung injury induced by lipopolysaccharide: a model for ARDS" *FASEB J.*, 2002, pp. 1713-1720, vol. 16.

Satoh, M. et al. "NAD(P)H oxidase and uncoupled nitric oxide synthase are major sources of glomerular superoxide in rats with experimental diabetic nephropathy" *Am. J. Physiol Renal Physiol*, 2005, pp. F1144-F1152, vol. 288.

Sharma, K. et al. "TGF-β impairs renal autoregulation via generation of ROS" *Am. J. Physiol Renal Physiol*, 2005, pp. F1069-F1079, vol. 288.

Sirker, A. et al. "Involvement of NADPH Oxidases in Cardiac Remodelling and Heart Failure" *Am. J. Nephrol*, 2007, pp. 649-660, vol. 27.

Sonta, T. et al. "Evidence for Contribution of Vascular NAD(P)H Oxidase to Increased Oxidative Stress in Animal Models of Diabetes and Obesity" *Free Radical Biology & Medicine*, 2004, pp. 115-123, vol. 37, No. 1.

Vaquero, V. C. et al. "Reactive Oxygen Species Produced by NAD(P)H Oxidase Inhibit Apoptosis in Pancreatic Cancer Cells" *The Journal of Biological Chemistry*, Aug. 13, 2004, pp. 34643-34654, vol. 279, No. 33.

Kerbel, R. S. "Tumor Angiogenesis" *N. Engl J Med*, May 8, 2008, pp. 2039-2049, vol. 358.

Banfi, B. et al. "NOX3, a Superoxide-generating NADPH Oxidase of the Inner Ear" *The Journal of Biological Chemistry*, Oct. 29, 2004, pp. 46065-46072, vol. 279, No. 44.

Laleu, B. et al. "First in Class, Potent, and Orally Bioavailable NADPH Oxidase Isoform 4 (Nox4) Inhibitors for the Treatment of Idiopathic Pulmonary Fibrosis" *J. Med. Chem.*, 2010, pp. 7715-7730, vol. 53.

Lambeth, J. D. et al. "NOX enzymes as novel targets for drug development" *Semin Immunopathol*, 2008, pp. 1-25.

Rao, P. V. et al. "Expression of nonphagocytic NADPH oxidase system in the ocular lens" *Molecular Vision*, 2004, pp. 112-121, vol. 10.

Vendrov, A. E. et al. "NADPH Oxidases Regulate CD44 and Hyaluronic Acid Expression in Thrombin-treated Vascular Smooth Muscle Cells and in Atherosclerosis" *The Journal of Biological Chemistry*, Aug. 20, 2010, pp. 26545-26557, vol. 285, No. 34.

Sedeek, M. et al. "Critical role of Nox4-based NADPH oxidase in glucose-induced oxidative stress in the kidney: implications in type 2 diabetic nephropathy" *Am. J. Physiol. Renal Physiol.*, 2010, pp. F1348-F1358, vol. 229.

Office Action dated Jun. 18, 2012 in U.S. Appl. No. 12/532,336.
Office Action dated Oct. 13, 2010 in U.S. Appl. No. 12/532,336.
Office Action dated Mar. 29, 2011 in U.S. Appl. No. 12/532,336.
Cancer [online], retrieved on Jul. 6, 2007, retrieved from the internet, URL: http://www.nim.nih.gov/medlineplus/cancer.html, pp. 1-10.

Junker, L. M. et al. "High-Throughput Screens for Small-Molecule Inhibitors of *Pseudomonas aeruginosa* Biofilm Development" *Antimicrobial Agents and Chemotherapy*, Oct. 2007, pp. 3582-3590, vol. 51, No. 10.

Dornow, A. et al. "Darstellung and Umsetzung einiger substituierter 3-Nitro-pyridine" *Chem. Ber.*, 1966, pp. 244-253, vol. 99.

Chemcats Accession No. 2029347921, Jun. 13, 2008, XP-002514328, p. 1.

Written Opinion in International Application No. PCT/IB2009/054148, Oct. 12, 2009, pp. 1-8.

Office Action dated Apr. 17, 2012 in U.S. Appl. No. 13/120,436.

Database CA [Online] Chemical Abstracts Service, Accession No. 2007:341007, 2007, XP-002558729, p. 1.

Database CA [Online] Chemical Abstracts Service, Accession No. 2004:14711, 2003, XP-002558730, pp. 1-2.

Written Opinion in International Application No. PCT/IB2009/054156, Mar. 3, 2010, pp. 1-10.

Ushio-Fukai, M. et al. "Reactive oxygen species and angiogenesis: NADPH oxidase as target for cancer therapy" *Cancer Letters*, 2008, pp. 37-52, vol. 266.

Chemcats Accession No. 2049339652, Jun. 13, 2008, XP-002514424, pp. 1-6.

Office Action dated Apr. 16, 2012 in U.S. Appl. No. 13/120,438.

Written Opinion in International Application No. PCT/IB2009/054155, Nov. 6, 2010, pp. 1-7.

Lala, P. K. et al. "Role of nitric oxide in tumor progression: Lessons from experimental tumors" *Cancer and Metastasis Reviews*, 1998, pp. 91-106, vol. 17.

Golub, T. R. et al. "Molecular Classification of Cancer: Class Discovery and Class Prediction by Gene Expression Monitoring" *Science*, Oct. 15, 1999, pp. 531-537, vol. 286.

Wolff, M. E. et al. "Burger's Medicinal Chemistry and Drug Discovery", 1994 Wiley-Interscience, Fifth Edition, vol. I: Principles and Practice, pp. 975-977.

"Derivative." Merriam-Webster Online Dictionary, 2010, accessed Apr. 20, 2010, http://merriam-webster.com/dictionary/derivative.

Written Opinion in International Application No. PCT/EP2008/053390, Jul. 21, 2008, pp. 1-6.

Written Opinion in International Application No. PCT/IB2009/054150, Oct. 13, 2010, pp. 1-11.

Abdelrahman, M. et al. "Inhibitors of NADPH Oxidase Reduce the Organ Injury in Hemorrhagic Shock" *Shock*, 2005, pp. 107-114, vol. 23, No. 2.

Anantharam, V. et al. "Pharmacological inhibition of neuronal NADPH oxidase protects against 1-methyl-4-phenylpyridinium (MPP+)-induced oxidative stress and apoptosis in mesencephalic dopaminergic neuronal cells" *NeuroToxicology*, 2007, pp. 988-997, vol. 28.

Puntambekar, P. et al. "Essential Role of Rac1/NADPH oxidase in nerve growth factor induction of TRPV1 expression" *Journal of Neurochemistry*, 2005, pp. 1689-1703, vol. 95.

Sturrock, A. et al. "Nox4 mediates TGF-β1-induced retinoblastoma protein phosphorylation, proliferaton, and hypertrophy in human airway smooth muscle cells" *Am. J Physiol. Lung. Cell Mol. Physiol.*, 2007, pp. L1543-L1555. vol. 292, No. 6.

Wu, D.-C. et al. "The inflammatory NADPh oxidase enzyme modulates motor neuron degeneration in amyotrophic lateral sclerosis mice" *PNAS*, Aug. 8, 2006, pp. 12132-12137, vol. 103, No. 32.

Klein, C. et al. CAS:147:427219, 2007, Accession No. 2007:1146277, pp. 1-4.

Slade, R. et al. CAS:144:412361, 2006, Accession No. 2006:361235, pp. 1-4.

Office Action dated Mar. 19, 2012 in U.S. Appl. No. 12/532,567.

Written Opinion in International Application No. PCT/EP2008/053704, Jul. 7, 2008, pp. 1-7.

Briones, A. M. et al. "Differential regulation of Nox1, Nox2 and Nox4 in vascular smooth muscle cells from WKY and SHR" *Journal of the American Society of Hypertension*, 2011, pp. 137-153, vol. 5, No. 3.

Musset, B. et al. "NOX5 in Human Spermatozoa" *The Journal of Biological Chemistry*, Mar. 16, 2012, pp. 9376-9388, vol. 287, No. 12.

(56) References Cited

OTHER PUBLICATIONS

Sedeek, M. et al. "Renoprotective effects of a novel Nox1/4 inhibitor in a mouse model of Type 2 diabetes" *Clinical Science*, 2013, pp. 191-202, vol. 124.
STN on the Web, File Registry, RN=914071-42-4 (Nov. 28, 2006), 909372-43-6 (Oct. 3, 2006), 908551-37-1 (Sep. 26, 2006), 906780-88-9 (Sep. 15, 2006), 906212-76-8 (Sep. 10, 2006), 906212-74-6 (Sep. 10, 2006), 906212-70-2 (Sep. 10, 2006), 906212-05-3 (Sep. 10, 2006), 899030-77-4 (Aug. 6, 2006), 899030-70-7 (Aug. 6, 2006), 899030-63-8 (Aug. 6, 2006), 899030-57-0 (Aug. 6, 2006), 899026-88-1 (Aug. 6, 2006), 899026-83-6 (Aug. 6, 2006), 899026-78-9 (Aug. 6, 2006), 899026-67-6 (Aug. 6, 2006), 899026-57-4 (Aug. 6, 2006), 899026-52-9 (Aug. 6, 2006), 899026-47-2 (Aug. 6, 2006), 899026-42-7 (Aug. 6, 2006), 899026-37-0 (Aug. 6, 2006), 899026-32-5 (Aug. 6, 2006), 899026-19-8 (Aug. 6, 2006), 897547-95-4 (Jul. 31, 2006), 897547-9-3-2 (Jul. 31, 2006), 897547-92-1 (Jul. 31, 2006), 897547-91-0 (Jul. 31, 2006), 897547,90-9 (Jul. 31, 2006), 896654-25-4 (Jul. 28, 2006), 896654-23-2 (Jul. 28, 2006), 896654-21-0 (Jul. 28, 2006), 896654-19-6 (Jul. 28, 2006), 896056-52-3 (Jul. 25, 2006), 896056-49-8 (Jul. 25, 2006), 896056-46-5 (Jul. 25, 2006), 895991-49-8 (Jul. 25, 2006), 895991-44-3 (Jul. 25, 2006), 895991-40-9 (Jul. 25, 2006), pp. 1-18.
STN on the Web, File Registry, RN=895991-35-2 (Jul. 25, 2006),895991-30-7 (Jul. 25, 2006),895991-25-0 (Jul. 25, 2006),895991-20-5 (Jul. 25, 2006),895991-15-8 (Jul. 25, 2006),895991-02-3 (Jul. 25, 2006),895990-97-3 (Jul. 25, 2006),895990-92-8 (Jul. 25, 2006),895990-73-5 (Jul. 25, 2006),895990-68-8 (Jul. 25, 2006),895990-54-2 (Jul. 25, 2006),895990-49-5 (Jul. 25, 2006),895990-40-6 (Jul. 25, 2006),890865-63-1 (Jul. 6, 2006), 885906-56-9 (May 29, 2006),885906-51-4 (May 29, 2006),885906-35-4 (May 29, 2006), 885906-31-0 (May 29, 2006),885906-27-4 (May 29, 2006),885906-21-8 (May 29, 2006),885890-49-3 (May 29, 2006),885888-49-5 (May 29, 2006),847586-98-5 (Mar. 30, 2005),847586-96-3 (Mar. 30, 2005),847586-86-1 (Mar. 30, 2005),847586-83-8 (Mar. 30, 2005),847586-82-7 (Mar. 30, 2005),847586-81-6 (Mar. 30, 2005),847586-74-7 (Mar. 30, 2005),847586-72-5 (Mar. 30, 2005),847586-69-0 (Mar. 30, 2005),847586-56-5 (Mar. 30, 2005),847586-51-0 (Mar. 30, 2005),847586-49-6 (Mar. 30, 2005),847586-42-9 (Mar. 30, 2005),847586-38-3 (Mar. 30, 2005),847586-36-1 (Mar. 30, 2005), pp. 1-20.
STN on the Web, File Registry, RN=847586-32-7 (Mar. 30, 2005),847586-30-5 (Mar. 30, 2005),847586-24-7 (Mar. 30, 2005),847586-23-6 (Mar. 30, 2005),847573-56-2 (Mar. 30, 2005),847573-45-9 (Mar. 30, 2005),847573-43-7 (Mar. 30, 2005),847573-41-5 (Mar. 30, 2005),847573-40-4 (Mar. 30, 2005),847573-35-7 (Mar. 30, 2005),847573-31-3 (Mar. 30, 2005),847573-25-5 (Mar. 30, 2005),847573-23-3 (Mar. 30, 2005),847573-13-1 (Mar. 30, 2005),847573-07-3 (Mar. 30, 2005),847572-88-7 (Mar. 30, 2005),847572-77-4 (Mar. 30, 2005),847572-75-2 (Mar. 30, 2005),847572-66-1 (Mar. 30, 2005),847572-61-6 (Mar. 30, 2005),847572-60-5 (Mar. 30, 2005),847572-57-0 (Mar. 30, 2005),847572-51-4 (Mar. 30, 2005),847572-38-7 (Mar. 30, 2005),847572-35-4 (Mar. 30, 2005),847572-33-2 (Mar. 30, 2005),727370-48-1 (Aug. 16 2004),669753-72-4 (Apr. 1, 2004),669753-67-7 (Apr. 1, 2004),669753-62-2 (Apr. 1, 2004),516455-29-1 (May 16, 2003), pp. 1-16.
ACS on STN Tokyo, Registry, RN=955327-56-7 (Nov. 21, 2007), 955327-53-4 (Nov. 21, 2007), 955327-50-1 (Nov. 21, 2007), 955327-47-6 (Nov. 21, 2007), 955327-44-3 (Nov. 21, 2007), 955285-61-7 (Nov. 21, 2007), 955285-55-9 (Nov. 21, 2007), 955285-49-1 (Nov. 21, 2007), 955265-43-5 (Nov. 21, 2007), 955272-06-7 (Nov. 21, 2007), 955285-37-7 (Nov. 21, 2007) pp. 1-6.
Asaba, K. et al. "Effects of NADPH oxidase inhibitor in diabetic nephropathy" *Kidney International*, 2005, pp. 1890-1898, vol. 67.
Baumer, A. T. et al. "The NAD(P)H Oxidase Inhibitor Apocynin Improves Endothelial NO/Superoxide Balance and Lowers Effectively Blood Pressure in Spontaneously Hypertensive Rats: Comparison to Calcium Channel Blockade" *Clinical and Experimental Hypertension*, 2007, pp. 287-299, vol. 29.
Chirino, Y. I. et al. "Protective effects of apocynin against cisplatin-induced oxidative stress and nephrotoxicity" *Tosicology*, 2008, pp. 18-23, vol. 245.
Chan, E. C. et al. "Regulation of cell proliferation by NADPH oxidase-mediated signaling: Potential roles in tissue repair, regenerative medicine and tissue engineering" *Pharmacology & Therapeutics*, 2009, pp. 97-108, vol. 122.
Jarman, E. R. et al. "An inhibitor of NADPH oxidase-4 attenuates established pulmonary fibrosis in a rodent disease model" *AJRCMB Articles in Press*, Aug. 26, 2013, pp. 1-30.
Lafeber, F. P. J. G. et al. "Apocynin, a plant-derived, cartilage-saving drug, might be useful in the treatment of rheumatoid arthritis" *Rheumatology*, 1999, pp. 1088-1093, vol. 38.
Peters, E. A. et al. "Effect of Apocynin on Ozone-Induced Airway Hyperresponsiveness to Methacholine in Asthmatics" *Free Radical Biology & Medicine*, 2001, pp. 1442-1447, vol. 31, No. 11.
Rachmilewitz, D. et al. "Sulphydryl blocker induced small intestinal inflammation in rats: a new model mimicking Crohn's disease" *Gut*, 1997, pp. 358-365, vol. 41.
Tang, X. N. et al. "Apocynin Improves Outcome in Experimental Stroke with a Narrow Dose Range" *Neuroscience*, 2008, pp. 556-562, vol. 154.
Wang, W. et al. "Effect of the NADPH Oxidase Inhibitor Apocynin on Septic Lung Injury in Guinea Pigs" *American Journal of Respiratory and Critical Care Medicine*, 1994, pp. 1449-1452, vol. 150.
Zhao, W. et al. "Kidney Fibrosis in Hypertensive Rats: Role of Oxidative Stress" *Am J Nephrol*, 2008, pp. 548-554, vol. 28.
Block, K. et al. "Subcellular localization of Nox4 and regulation in diabetes" *PNAS*, Aug. 25, 2009, pp. 14385-14390, vol. 106, No. 34.
De Minicis, S. et al. "Oxidative stress in alcoholic liver disease: Role of NADPH oxidase complex" *Journal of Gastroenterology and Hepatology*, 2008, pp. S98-S103, Supp 1, No. 23.
Forbes, J. M. et al. "Diabetic Nephropathy: Where Hemodynamics Meets Metabolism" *Exp Clin Endocrinol Diabetes*, 2007, pp. 1-16.
Gorin, Y. et al. "Nox4 NAD(P)H Oxidase Mediates Hypertrophy and Fibronectin Expression in the Diabetic Kidney" *The Journal of Biological Chemistry*, Nov. 25, 2005, pp. 39616-39626, vol. 280, No. 47.
Guichard, C. et al. "NOX family NADPH oxidases in liver and in pancreatic islets: a role in the metabolic syndrome and diabetes?" *Biochemical Society Transactions*, 2008, pp. 920-929, vol. 36.
Jiang, J. et al. "Apoptotic body engulfment by hepatic stellate cells promotes their survival by the JAK/STAT and Akt/NF-κB-dependent pathways" *J Hepatol.*, Jul. 2009, pp. 139-148, vol. 51. No. 1.
Kakehi, T. et al. "NOX enzymes and diabetic complications" *Semin Immunopathol*, 2008, pp. 301-314, vol. 30.
Lambeth, D. "Nox Enzymes, ROS, and Chronic Disease: An Example of Antagonistic Pleiotropy" *Free Radic Biol Med.*, Aug. 2007, pp. 332-347, vol. 43, No. 3.
Nam, S. M. et al. "Effects of NADPH oxidase inhibitor on diabetic nephropathy in OLETF rats: The role of reducing oxidative stress in its protective property" *Diabetes Research and Clinical Practice*, 2009, pp. 176-182, vol. 83.
Tojo, A. et al. "Suppressing renal NADPH oxidase to treat diabetic nephropathy" *Expert Opin. Ther. Targets*, 2007, pp. 1011-1018, vol. 11, No. 8.
Currently pending claims of U.S. Appl. No. 13/734,205, Jan. 4, 2013.
Currently pending claims of U.S. Appl. No. 13/755,387, Jan. 31, 2013.
Currently pending claims of U.S. Appl. No. 13/755,617, Jan. 31, 2013.
Currently pending claims of U.S. Appl. No. 13/120,440, Mar. 23, 2011.
Englert, S. M. et al. "Pyrazolones Derived from the Carbethoxypiperidones" *Journal of American Chemical Society*, Mar. 1934, pp. 700-702, vol. 56.
Carpino, P. et al. "Pyrazolinone-piperidine Dipeptide Growth Hormone Secretagogues (GHSs): Discovery of Capromorelin" *Bioorganic & Medicinal Chemistry*, Feb. 20, 2003, pp. 581-590, vol. 11, No. 4.

(56) References Cited

OTHER PUBLICATIONS

Carpino, P. et al. "Discovery and Biological Characterization of Capromorelin Analogues with Extended Half-Lives" *Bioorganic & Medicinal Chemistry Letters*, Nov. 18, 2002, pp. 3279-3282, vol. 12, No. 22.

Guillou, S. et al. "N-arylation of 3-alkoxypyrazoles, the case of the pyridines" *Tetrahedron*, Feb. 10, 2010, pp. 654-2663, vol. 66, No. 14.

Leto, T. L. et al. "Role of Nox Family NADPH Oxidases in Host Defense" *Antioxidants & Redox Signaling*, 2006, pp. 1549-1561, vol. 8, Nos. 9-10.

Cheng, G. et al. "Homologs of gp91*phox*: cloning and tissue expression of Nox3, Nox4, and Nox5" *Gene*, 2001, pp. 131-140, vol. 269.

Written Opinion in International Application No. PCT/IB2011/050668, Jul. 11, 2011, pp. 1-9.

Krehan, D. et al. "Aza-THIP and Related Analogues of THIP as $GABA_C$ Antagonists" *Bioorganic & Medicinal Chemistry*, Jan. 1, 2003, pp. 4891-4896, vol. 11.

Database CA [Online], Chemical Abstract Accession No. 1977:155590, Ozdowska, Z. "New derivatives of N-benzyl-4-carbethoxy-3-piperidone" *Roczniki Chemii*, 1976, pp. 1-2, vol. 50, No. 10, XP-002598501.

Aoyama, T. et al. "Nicotinamide Adenine Dinucleotide Phosphate Oxidase in Experimental Liver Fibrosis: GKT137831 as a Novel Potential Therapeutic Agent" *Hepatology*, 2012, pp. 2316-2327, vol. 56, No. 6.

Jiang, J. X. et al. "Liver fibrosis and hepatocyte apoptosis are attenuated by GKT137831, a novel NOX4/NOX1 inhibitor in vivo" *Free Radical Biology and Medicine*, 2012, pp. 289-296, vol. 53.

Green, D. E. et al. "The Nox4 Inhibitor GKT137831 Attenuates Hypoxia-Induced Pulmonary Vascular Cell Proliferation" *American Journal of Respiratory Cell and Molecular Biology*, Nov. 2012, pp. 718-726, vol. 47, Issue 5.

Gray, S. P. et al. "NADPH Oxidase 1 Plays a Key Role in Diabetes Mellitus-Accelerated Atherosclerosis" *Circulation*, May 7, 2013, pp. 1888-1902.

Wilkinson-Berka, J. et al. "NADPH Oxidase, NOX1, Mediates Vascular Injury in Ischemic Retinopathy" *Antioxidants & Redox Signaling*, 2013, pp. 1-15.

STN on the Web, File Registry, RN=727370-48-1 (Aug. 16, 2004), 890865-63-1 (Jul. 6, 2006), p. 1.

Written Opinion in International Application No. PCT/IB2011/050667, Jun. 22, 2011, pp. 1-8.

Currently pending claims of U.S. Appl. No. 13/935,667, Jul. 5, 2013.

\* cited by examiner

PYRAZOLINE DIONE DERIVATIVES AS NADPH OXIDASE INHIBITORS

CROSS-REFERENCE TO RELATED APPLICATION

This application is the U.S. national stage application of International Patent Application No. PCT/IB2010/054329, filed Sep. 27, 2010.

FIELD OF THE INVENTION

The present invention relates to pyrazoline dione derivatives of Formula (I), pharmaceutical composition thereof and to their use for the preparation of a medicament for the treatment and/or prophylaxis of cardiovascular diseases, respiratory disorders, disorders affecting the metabolism, skin and/or bone diseases, neurodegenerative diseases, kidney diseases, reproduction disorders, inflammatory disorders and cancers. Specifically, the present invention is related to pyrazoline dione derivatives useful for the preparation of a pharmaceutical formulation for the modulation, notably the inhibition of the activity or function of the Nicotinamide adenine dinucleotide phosphate oxidase (NADPH Oxidase).

BACKGROUND OF THE INVENTION

NADPH oxidases (NOX) are proteins that transfer electrons across biological membranes. In general, the electron acceptor is oxygen and the product of the electron transfer reaction is superoxide. The biological function of NOX enzymes is therefore the generation of reactive oxygen species (ROS) from oxygen. Reactive oxygen species (ROS) are oxygen-derived small molecules, including oxygen radicals (super-oxide anion [$.O_2^-$], hydroxyl [HO.], peroxyl [ROO.], alkoxyl [RO.] and hydroperoxyl [HOO.]) and certain non-radicals that are either oxidizing agents and/or are easily converted into radicals. Nitrogen-containing oxidizing agents, such as nitric oxide are also called reactive nitrogen species (RNS). ROS generation is generally a cascade of reactions that starts with the production of superoxide. Superoxide rapidly dismutates to hydrogen peroxide either spontaneously, particularly at low pH or catalyzed by superoxide dismutase. Other elements in the cascade of ROS generation include the reaction of superoxide with nitric oxide to form peroxynitrite, the peroxidase-catalyzed formation of hypochlorous acid from hydrogen peroxide, and the iron-catalyzed Fenton reaction leading to the generation of hydroxyl radical.

ROS avidly interact with a large number of molecules including other small inorganic molecules as well as DNA, proteins, lipids, carbohydrates and nucleic acids. This initial reaction may generate a second radical, thus multiplying the potential damage. ROS are involved not only in cellular damage and killing of pathogens, but also in a large number of reversible regulatory processes in virtually all cells and tissues. However, despite the importance of ROS in the regulation of fundamental physiological processes, ROS production can also irreversibly destroy or alter the function of the target molecule. Consequently, ROS have been increasingly identified as major contributors to damage in biological organisms, so-called "oxidative stress".

During inflammation, NADPH oxidase is one of the most important sources of ROS production in vascular cells under inflammatory conditions (Thabut et al., 2002, *J. Biol. Chem.*, 277:22814-22821).

In the lung, tissues are constantly exposed to oxidants that are generated either endogenously by metabolic reactions (e.g. by mitochondrial respiration or activation of recruited inflammatory cells) or exogenously in the air (e.g. cigarette smoke or air pollutants). Further, the lungs, constantly exposed to high oxygen tensions as compared to other tissues, have a considerable surface area and blood supply and are particularly susceptible to injury mediated by ROS (Brigham, 1986, *Chest*, 89(6): 859-863). NADPH oxidase-dependent ROS generation has been described in pulmonary endothelial cells and smooth muscle cells. NADPH oxidase activation in response to stimuli has been thought to be involved in the development of respiratory disorders such as pulmonary hypertension and enhancement of pulmonary vasoconstriction (Djordjevic et al., 2005, *Arterioscler. Thromb. Vasc. Biol.*, 25, 519-525; Liu et al., 2004, *Am. J. Physiol. Lung, Cell. Mol. Physiol.*, 287: L111-118). Further, pulmonary fibrosis has been characterized by lung inflammation and excessive generation of ROS.

Osteoclasts, which are macrophage-like cells that play a crucial role in bone turn-over (e.g. bone resorption), generate ROS through NADPH oxidase-dependent mechanisms (Yang et al., 2002, *J. Cell. Chem.* 84, 645-654).

Diabetes is known to increase oxidative stress (e.g. increased generation of ROS by auto-oxidation of glucose) both in humans and animals and increased oxidative stress has been said to play an important role in the development of diabetic complications. It has been shown that increased peroxide localization and endothelial cell dysfunction in the central retina of diabetic rats coincides with the areas of NADPH oxidase activity in the retinal endothelial cells (Ellis et al., 2000, *Free Rad. Biol. Med.*, 28:91-101). Further, it has been suggested that controlling oxidative stress (ROS) in mitochondria and/or inflammation may be a beneficial approach for the treatment of diabetes (Pillarisetti et al., 2004, *Expert Opin. Ther. Targets*, 8(5):401-408).

ROS are also strongly implicated in the pathogenesis of atherosclerosis, cell proliferation, hypertension and reperfusion injury cardiovascular diseases in general (Cai et al., 2003, *Trends Pharmacol. Sci.*, 24:471-478). Not only is superoxide production, for example in the arterial wall, increased by all risk factors for atherosclerosis, but ROS also induce many "proatherogenic" in vitro cellular responses. An important consequence of the formation of ROS in vascular cells is the consumption of nitric oxide (NO). NO inhibits the development of vascular diseases, and loss of NO is important in the pathogenesis of cardiovascular diseases. The increase in NADPH oxidase activity in vascular wall after balloon injury has been reported (Shi et al., 2001, *Throm. Vasc. Biol.*, 2001, 21, 739-745)

It is believed that oxidative stress or free radical damage is also a major causative factor in neurodegenerative diseases. Such damages may include mitochondrial abnormalities, neuronal demyelination, apoptosis, neuronal death and reduced cognitive performance, potentially leading to the development of progressive neurodegenerative disorders (Nunomura et al., 2001, *J. Neuropathol. Exp. Neurol.*, 60: 759-767; Girouard, 2006, *J. Appl. Physiol.* 100:328-335).

Further, the generation of ROS by sperm has been demonstrated in a large number of species and has been suggested to be attributed to an NADPH oxidase within spermatozoa (Vernet et al., *Biol. Reprod.*, 2001, 65:1102-1113). Excessive ROS generation has been suggested to be implicated in sperm pathology, including male infertility and also in some penile disorders and prostate cancer.

NADPH oxidases are multi-subunit enzymes made up of a membrane-bound cytochrome b558 domain and three cytosolic protein subunits, p47phox, p67phox and a small GTPase, Rac. Seven isoforms of NOX enzymes have been identified including NOX1, NOX2, NOX3, NOX4, NOX5, DUOX1 and DUOX2 (Leto et al., 2006, *Antioxid Redox Signal*, 8(9-10):1549-61; Cheng et al., 2001, *Gene*, 16; 269(1-2):131-40).

Thus, ROS derived from NADPH contribute to the pathogenesis of numerous diseases, especially cardiovascular diseases or disorders, respiratory disorder or disease, disease or disorder affecting the metabolism, bone disorders, neurodegenerative diseases, inflammatory diseases, reproduction disorder or disease, pain, cancer and disease or disorders of the gastrointestinal system. Therefore, it would be highly desirable to develop new active agents focusing on the ROS signalling cascade, especially on NADPH oxidases (NOX).

SUMMARY OF THE INVENTION

The present invention is directed towards new molecules useful in the treatment and/or prophylaxis of Nicotinamide adenine dinucleotide phosphate oxidase (NADPH Oxidase) related disorders such as cardiovascular diseases, respiratory disorders, disorders affecting the metabolism, skin and/or bone diseases, neurodegenerative diseases, kidney diseases, reproduction disorders, inflammatory disorders, cancers, allergic disorders, traumatisms, septic, hemorrhagic and anaphylactic shock, diseases or disorders of the gastrointestinal system, angiogenesis and angiogenesis-dependent conditions. Notably, the invention is related to new molecules useful in the inhibition or reduction of ROS production in cells.

A first aspect of the invention provides a pyrazoline dione derivative according to Formula (I), wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, X and n are as defined below, as well as pharmaceutically acceptable salts and pharmaceutically active derivative thereof.

A second aspect of the invention relates to a pyrazoline dione derivative according to Formula (I), wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, X and n are as defined below, as well as pharmaceutically acceptable salts and pharmaceutically active derivative thereof for use as a medicament.

A third aspect of the invention relates to a pharmaceutical composition containing at least one a pyrazoline dione derivative according to the invention, as well as pharmaceutically acceptable salts and pharmaceutically active derivative thereof and a pharmaceutically acceptable carrier, diluent or excipient thereof.

A fourth aspect of the invention resides in a use of a pyrazoline dione derivative according to the invention as well as pharmaceutically acceptable salts and pharmaceutically active derivative thereof for the preparation of a pharmaceutical composition for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system, angiogenesis and angiogenesis-dependent and/or other diseases and disorders associated with Nicotinamide adenine dinucleotide phosphate oxidase (NADPH Oxidase).

A fifth aspect of the invention relates to a method for treating a patient suffering from a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system, angiogenesis and angiogenesis-dependent and other diseases and/or disorders associated with Nicotinamide adenine dinucleotide phosphate oxidase (NADPH Oxidase). The method comprises administering a pyrazoline dione derivative according to Formula (I), wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, X and n are defined below, as well as pharmaceutically acceptable salts and pharmaceutically active derivative thereof in a patient in need thereof.

A sixth aspect of the invention relates to a pyrazoline dione derivative according to Formula (I), wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, X and n are as defined below, as well as pharmaceutically acceptable salts and pharmaceutically active derivative thereof, for the treatment of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system, angiogenesis and angiogenesis-dependent and other diseases and/or disorders associated with Nicotinamide adenine dinucleotide phosphate oxidase (NADPH Oxidase).

A seventh aspect of the invention relates to a pyrazoline dione derivative intermediate according to Formula (II) according to the invention.

An eighth aspect of the invention relates to a process for the preparation of an intermediate of Formula (II) according to the invention.

A ninth aspect of the invention relates to a process for the preparation of a pyrazoline dione derivative according to Formula (I) wherein $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, X and n are as defined below and $R^2$ is H.

A tenth aspect of the invention relates to a process for the preparation of a pyrazoline dione derivative according to Formula (I) wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, X and n are as defined below.

Other features and advantages of the invention will be apparent from the following detailed description.

DETAILED DESCRIPTION OF THE INVENTION

The following paragraphs provide definitions of the various chemical moieties that make up the compounds according to the invention and are intended to apply uniformly through-out the specification and claims, unless an otherwise expressly set out definition provides a broader definition.

The term "alkyl" when used alone or in combination with other terms, comprises a straight chain or branched $C_1$-$C_{20}$ alkyl which refers to monovalent alkyl groups having 1 to 20 carbon atoms. This term is exemplified by groups such as methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, n-heptyl, 2-methylhexyl, 3-methylhexyl, 4-methylhexyl, 5-methylhexyl, n-heptyl, n-octyl, n-nonyl, n-decyl, tetrahydrogeranyl, n-dodecyl, n-tridecyl, n-tetradecyl, n-pentadecyl, n-hexadecyl, n-octadecyl, n-nonadecyl, and n-eicosanyl and the like. Preferably, these include $C_1$-$C_9$ alkyl, more preferably $C_1$-$C_6$ alkyl, especially preferably $C_1$-$C_4$ alkyl, which, by analogy, refer respectively to monovalent alkyl groups having 1 to 9 carbon atoms, monovalent alkyl groups having 1 to 6 carbon atoms and monovalent alkyl groups having 1 to 4 carbon atoms. Particularly, those include $C_1$-$C_6$ alkyl.

The term "alkenyl" when used alone or in combination with other terms, comprises a straight chain or branched $C_2$-$C_{20}$ alkenyl. It may have any available number of double bonds in any available positions, and the configuration of the double bond may be the (E) or (Z) configuration. This term is exemplified by groups such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 1-heptenyl, 1-octenyl, geranyl, 1-decenyl, 1-tetradecenyl, 1-octadecenyl, 9-octadecenyl, 1-eicosenyl, and 3,7,11,15-tetramethyl-1-hexadecenyl, and the like. Preferably, these include $C_2$-$C_8$ alkenyl, more preferably $C_2$-$C_6$ alkenyl. Among others, especially preferred are vinyl or ethenyl (—CH=$CH_2$), n-2-propenyl (allyl, —$CH_2$CH=$CH_2$), isopropenyl, 1-propenyl, 2-methyl-1-propenyl, 1-butenyl, 2-butenyl, and 3-methyl-2-butenyl and the like.

The term "alkynyl" when used alone or in combination with other terms, comprises a straight chain or branched $C_2$-$C_{20}$ alkynyl. It may have any available number of triple bonds in any available positions. This term is exemplified by groups such as alkynyl groups that may have a carbon number of 2-20, and optionally a double bond, such as ethynyl (—C≡CH), 1-propynyl, 2-propynyl (propargyl: —$CH_2$C≡CH), 2-butynyl, 2-pentene-4-ynyl, and the like. Particularly, these include $C_2$-$C_8$ alkynyl, more preferably $C_2$-$C_6$ alkynyl and the like. Preferably those include $C_2$-$C_6$ alkynyl which refers to groups having 2 to 6 carbon atoms and having at least 1 or 2 sites of alkynyl unsaturation.

The term "heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl and the like.

The term "aryl" refers to an unsaturated aromatic carbocyclic group of from 6 to 14 carbon atoms having a single ring (e.g., phenyl) or multiple condensed rings (e.g., indenyl, naphthyl). Aryl include phenyl, naphthyl, anthryl, phenanthrenyl and the like.

The term "$C_1$-$C_6$ alkyl aryl" refers to aryl groups having an $C_1$-$C_6$ alkyl substituent, including methyl phenyl, ethyl phenyl and the like.

The term "aryl $C_1$-$C_6$ alkyl" refers to $C_1$-$C_6$ alkyl groups having an aryl substituent, including 3-phenylpropanyl, benzyl and the like.

The term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

The term "$C_1$-$C_6$ alkyl heteroaryl" refers to heteroaryl groups having a $C_1$-$C_6$ alkyl substituent, including methyl furyl and the like.

The term "heteroaryl $C_1$-$C_6$ alkyl" refers to $C_1$-$C_6$ alkyl groups having a heteroaryl substituent, including furyl methyl and the like.

The term "$C_2$-$C_6$ alkenyl aryl" refers to an aryl groups having a $C_2$-$C_6$ alkenyl substituent, including vinyl phenyl and the like.

The term "aryl $C_2$-$C_6$ alkenyl" refers to a $C_2$-$C_6$ alkenyl groups having an aryl substituent, including phenyl vinyl and the like.

The term "$C_2$-$C_6$ alkenyl heteroaryl" refers to heteroaryl groups having a $C_2$-$C_6$ alkenyl substituent, including vinyl pyridinyl and the like.

The term "heteroaryl $C_2$-$C_6$ alkenyl" refers to $C_1$-$C_6$ alkenyl groups having a heteroaryl substituent, including pyridinyl vinyl and the like.

The term "$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl includes cyclopentyl, cyclohexyl, norbornyl and the like.

The term "heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidinyl, piperidinyl, piperazinyl, morpholinyl, tetrahydrofuranyl and the like.

The term "$C_1$-$C_6$ alkyl $C_3$-$C_8$-cycloalkyl" refers to $C_3$-$C_8$-cycloalkyl groups having a $C_1$-$C_6$ alkyl substituent, including methyl cyclopentyl and the like.

The term "$C_3$-$C_8$-cycloalkyl $C_1$-$C_6$ alkyl" refers to $C_1$-$C_6$ alkyl groups having a $C_3$-$C_8$-cycloalkyl substituent, including 3-cyclopentyl propyl and the like.

The term "$C_1$-$C_6$ alkyl heterocycloalkyl" refers to heterocycloalkyl groups having a $C_1$-$C_6$ alkyl substituent, including 4-methylpiperidinyl and the like.

The term "heterocycloalkyl $C_1$-$C_6$ alkyl" refers to $C_1$-$C_6$ alkyl groups having a heterocycloalkyl substituent, including (1-methylpiperidin-4-yl)methyl and the like.

The term "carboxy" refers to the group —C(O)OH.

The term "carboxy $C_1$-$C_6$ alkyl" refers to $C_1$-$C_6$ alkyl groups having a carboxy substituent, including 2-carboxyethyl and the like.

The term "acyl" refers to the group —C(O)R where R includes H, "alkyl," preferably "$C_1$-$C_6$ alkyl," "aryl," "heteroaryl," "$C_3$-$C_8$-cycloalkyl," "heterocycloalkyl," "aryl $C_1$-$C_6$ alkyl," "heteroaryl $C_1$-$C_6$ alkyl," "$C_3$-$C_8$-cycloalkyl $C_1$-$C_6$ alkyl" or "heterocycloalkyl $C_1$-$C_6$ alkyl", including acetyl and the like.

The term "acyl $C_1$-$C_6$ alkyl" to $C_1$-$C_6$ alkyl groups having an acyl substituent, including 2-acetylethyl and the like.

The term "acyl aryl" refers to aryl groups having an acyl substituent, including 2-acetylphenyl and the like.

The term "acyloxy" refers to the group —OC(O)R where R includes H, "$C_1$-$C_6$ alkyl", "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl,"

"heteroaryl $C_2$-$C_6$ alkynyl," "$C_3$-$C_8$-cycloalkyl $C_1$-$C_6$ alkyl," or "heterocycloalkyl $C_1$-$C_6$ alkyl", including acetyloxy and the like.

The term "acyloxy $C_1$-$C_6$ alkyl" refers to $C_1$-$C_6$ alkyl groups having an acyloxy substituent, including 2-(ethylcarbonyloxy)ethyl and the like.

The term "alkoxy" refers to the group —O—R where R includes "$C_1$-$C_6$ alkyl", "aryl", "heteroaryl", "aryl $C_1$-$C_6$ alkyl" or "heteroaryl $C_1$-$C_6$ alkyl". Preferred alkoxy groups include for example, methoxy, ethoxy, phenoxy and the like.

The term "alkoxy $C_1$-$C_6$ alkyl" refers to $C_1$-$C_6$ alkyl groups having an alkoxy substituent, including methoxyethyl and the like.

The term "alkoxycarbonyl" refers to the group —C(O)OR where R includes "$C_1$-$C_6$ alkyl", "aryl", "heteroaryl", "aryl $C_1$-$C_6$ alkyl", "heteroaryl $C_1$-$C_6$ alkyl" or "heteroalkyl".

The term "alkoxycarbonyl $C_1$-$C_6$ alkyl" refers to $C_1$-$C_6$ alkyl groups having an alkoxycarbonyl substituent, including 2-(benzyloxycarbonyl)ethyl and the like.

The term "aminocarbonyl" refers to the group —C(O)NRR' where R and R' are independently H, $C_1$-$C_6$ alkyl, aryl, heteroaryl, "aryl $C_1$-$C_6$ alkyl" or "heteroaryl $C_1$-$C_6$ alkyl," including N-phenyl carbonyl and the like.

The term "aminocarbonyl $C_1$-$C_6$ alkyl" refers to alkyl groups having an aminocarbonyl substituent, including 2-(dimethylaminocarbonyl)ethyl, N-ethyl acetamidyl, N,N-Diethyl-acetamidyl and the like.

The term "acylamino" refers to the group —NRC(O)R' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl," "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl", including acetylamino and the like.

The term "acylamino $C_1$-$C_6$ alkyl" refers to $C_1$-$C_6$ alkyl groups having an acylamino substituent, including 2-(propionylamino)ethyl and the like.

The term "ureido" refers to the group —NRC(O)NR'R" where R, R' and R" are independently H, "$C_1$-$C_6$ alkyl," "alkenyl," "alkynyl," "$C_3$-$C_8$-cycloalkyl," "heterocycloalkyl," "$C_1$-$C_6$ aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl," and where R' and R," together with the nitrogen atom to which they are attached, can optionally form a 3-8-membered heterocycloalkyl ring.

The term "ureido $C_1$-$C_6$ alkyl" refers to $C_1$-$C_6$ alkyl groups having an ureido substituent, including 2-(N'-methylureido)ethyl and the like.

The term "carbamate" refers to the group —NRC(O)OR' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "$C_1$-$C_6$ alkyl aryl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl" and optionally R can also be hydrogen.

The term "amino" refers to the group —NRR' where R and R' are independently H, "$C_1$-$C_6$ alkyl", "aryl", "heteroaryl", "$C_1$-$C_6$ alkyl aryl", "$C_1$-$C_6$ alkyl heteroaryl," "cycloalkyl," or "heterocycloalkyl," and where R and R', together with the nitrogen atom to which they are attached, can optionally form a 3-8-membered heterocycloalkyl ring.

The term "amino alkyl" refers to alkyl groups having an amino substituent, including 2-(1-pyrrolidinyl)ethyl and the like.

The term "ammonium" refers to a positively charged group —N⁺RR'R" where R, R' and R" are independently "$C_1$-$C_6$ alkyl", "$C_1$-$C_6$ alkyl aryl", "$C_1$-$C_6$ alkyl heteroaryl," "cycloalkyl," or "heterocycloalkyl," and where R and R', together with the nitrogen atom to which they are attached, can optionally form a 3-8-membered heterocycloalkyl ring.

The term "ammonium alkyl" refers to alkyl groups having an ammonium substituent, including 1-ethylpyrrolidinium and the like.

The term "halogen" refers to fluoro, chloro, bromo and iodo atoms.

The term "sulfonyloxy" refers to a group —OSO$_2$—R wherein R is selected from "$C_1$-$C_6$ alkyl," "$C_1$-$C_6$ alkyl" substituted with halogens, e.g., an —OSO$_2$—CF$_3$ group, "$C_2$-$C_6$ alkenyl," "alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl alkyl".

The term "sulfonyloxy $C_1$-$C_6$ alkyl" refers to alkyl groups having a sulfonyloxy substituent, including 2-(methylsulfonyloxy)ethyl and the like.

The term "sulfonyl" refers to group "—SO$_2$—R" wherein R is selected from "aryl," "heteroaryl," "$C_1$-$C_6$ alkyl," "$C_1$-$C_6$ alkyl" substituted with halogens, e.g., an —SO$_2$—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl".

The term "sulfonyl $C_1$-$C_6$ alkyl" refers to alkyl groups having a sulfonyl substituent, including 2-(methylsulfonyl)ethyl and the like.

The term "sulfinyl" refers to a group "—S(O)—R" wherein R is selected from "alkyl," "alkyl" substituted with halogens, e.g., a —SO—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfinyl alkyl" refers to alkyl groups having a sulfinyl substituent, including 2-(methylsulfinyl)ethyl and the like.

The term "sulfanyl" refers to groups —S—R where R includes H, "$C_1$-$C_6$ alkyl," "$C_1$-$C_6$ alkyl" substituted with halogens, e.g., a —S—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "alkynylheteroaryl," "cycloalkyl $C_1$-$C_6$ alkyl," or "heterocycloalkyl $C_1$-$C_6$ alkyl". Preferred sulfanyl groups include methylsulfanyl, ethylsulfanyl, and the like.

The term "sulfanyl $C_1$-$C_6$ alkyl" refers to $C_1$-$C_5$-alkyl groups having a sulfanyl substituent, including 2-(ethylsulfanyl)ethyl and the like.

The term "sulfonylamino" refers to a group —NRSO$_2$—R' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfonylamino $C_1$-$C_6$ alkyl" refers to alkyl groups having a sulfonylamino substituent, including 2-(ethylsulfonylamino)ethyl and the like.

The term "aminosulfonyl" refers to a group —$SO_2$—NRR' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", and where R and R', together with the nitrogen atom to which they are attached, can optionally form a 3-8-membered heterocycloalkyl ring. Aminosulfonyl groups include cyclohexylaminosulfonyl, piperidinylsulfonyl and the like.

The term "aminosulfonyl $C_1$-$C_6$ alkyl" refers to $C_1$-$C_6$ alkyl groups having an aminosulfonyl substituent, including 2-(cyclohexylaminosulfonyl)ethyl and the like.

Unless otherwise constrained by the definition of the individual substituent, all the above substituents should be understood as being all optionally substituted.

Unless otherwise constrained by the definition of the individual substituent, the term "substituted" refers to groups substituted with from 1 to 5 substituents selected from the group consisting of "$C_1$-$C_6$ alkyl," "$C_2$-$C_6$ alkenyl," "$C_2$-$C_6$ alkynyl," "$C_3$-$C_8$-cycloalkyl," "heterocycloalkyl," "$C_1$-$C_6$ alkyl aryl," "$C_1$-$C_6$ alkyl heteroaryl," "$C_1$-$C_6$ alkyl cycloalkyl," "$C_1$-$C_6$ alkyl heterocycloalkyl," "amino," "aminosulfonyl," "ammonium," "acyl amino," "amino carbonyl," "aryl," "heteroaryl," "sulfinyl," "sulfonyl," "alkoxy," "alkoxy carbonyl," "carbamate," "sulfanyl," "halogen," trihalomethyl, cyano, hydroxy, mercapto, nitro, and the like.

The term "pharmaceutically acceptable salts or complexes" refers to salts or complexes of the below-specified compounds of Formula (I). Examples of such salts include, but are not restricted, to base addition salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein.

The term "indirectly" also encompasses prodrugs which may be converted to the active form of the drug via endogenous enzymes or metabolism. The prodrug is a derivative of the compound according to the invention and presenting NADPH oxidase inhibiting activity that has a chemically or metabolically decomposable group, and a compound that may be converted into a pharmaceutically active compound in vivo by solvolysis under physiological conditions. The invention further encompasses any tautomers of the compounds according to the invention.

The term "cardiovascular disorder or disease" comprises atherosclerosis, especially diseases or disorders associated with endothelial dysfunction including but not limited to hypertension, cardiovascular complications of Type I or Type II diabetes, intimal hyperplasia, coronary heart disease, cerebral, coronary or arterial vasospasm, endothelial dysfunction, heart failure including congestive heart failure, peripheral artery disease, restenosis, trauma caused by a stent, stroke, ischemic attack, vascular complications such as after organ transplantation, myocardial infarction, hypertension, formation of atherosclerotic plaques, platelet aggregation, angina pectoris, aneurysm, aortic dissection, ischemic heart disease, cardiac hypertrophy, pulmonary embolus, thrombotic events including deep vein thrombosis, injury caused after ischemia by restoration of blood flow or oxygen delivery as in organ transplantation, open heart surgery, angioplasty, hemorrhagic shock, angioplasty of ischemic organs including heart, brain, liver, kidney, retina and bowel.

The term "respiratory disorder or disease" comprises bronchial asthma, bronchitis, allergic rhinitis, adult respiratory syndrome, cystic fibrosis, lung viral infection (influenza), pulmonary hypertension, idiopathic pulmonary fibrosis and chronic obstructive pulmonary diseases (COPD).

The term "allergic disorder" includes hay fever and asthma.

The term "traumatism" includes polytraumatism.

The term "disease or disorder affecting the metabolism" includes obesity, metabolic syndrome and Type II diabetes.

The term "skin disease" or disorder" includes psoriasis, eczema, dermatitis, wound healing and scar formation.

The term "bone disorder" includes osteoporosis, osteoporasis, osteosclerosis, periodontitis, and hyperparathyroidism.

The term "neurodegenerative disease or disorder" comprises a disease or a state characterized by a central nervous system (CNS) degeneration or alteration, especially at the level of the neurons such as Alzheimer's disease, Parkinson's disease, Huntington's disease, amyotrophic lateral sclerosis, epilepsy and muscular dystrophy. It further comprises neuroinflammatory and demyelinating states or diseases such as leukoencephalopathies, and leukodystrophies.

The term "demyelinating" is referring to a state or a disease of the CNS comprising the degradation of the myelin around the axons. In the context of the invention, the term demyelinating disease is intended to comprise conditions which comprise a process that demyelinate cells such as multiple sclerosis, progressive multifocal leukoencephalopathy (PML), myelopathies, any neuroinflammatory condition involving autoreactive leukocyte within the CNS, congenital metabolic disorder, a neuropathy with abnormal myelination, drug induced demyelination, radiation induced demyelination, a hereditary demyelinating condition, a prion induced demyelinating condition, encephalitis induced demyelination or a spinal cord injury. Preferably, the condition is multiple sclerosis.

The term "kidney disease or disorder" includes diabetic nephropathy, renal failure, glomerulonephritis, nephrotoxicity of aminoglycosides and platinum compounds and hyperactive bladder. In a particular embodiment, the term according to the invention includes chronic kidney diseases or disorders.

The term "reproduction disorder or disease" includes erectile dysfunction, fertility disorders, prostatic hypertrophy and benign prostatic hypertrophy.

The term "disease or disorder affecting the eye and/or the lens" includes cataract including diabetic cataract, re-opacification of the lens post cataract surgery, diabetic and other forms of retinopathy.

The term "conditions affecting the inner ear" includes presbyacusis, tinnitus, Meniere's disease and other balance problems, utriculolithiasis, vestibular migraine, and noise induced hearing loss and drug induced hearing loss (ototoxicity).

The term "inflammatory disorder or disease" means inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, heart failure, myocardial infarction, psoriasis, cystic fibrosis, stroke, acute bronchitis, chronic bronchitis, acute bronchiolitis, chronic bronchiolitis, osteoarthritis, gout, myelitis, ankylosing spondylitis, Reuter syndrome, psoriatic arthritis, spondylarthritis, juvenile arthritis or juvenile ankylosing spondylitis, reactive arthritis, infectious arthritis or arthritis after infection, gonococcal arthritis, syphilitic arthritis, Lyme disease, arthritis induced by "angiitis syndrome," polyarteritis nodosa, anaphylactic angiitis, Luegenec granulomatosis, rheumatoid polymyalgia, articular cell rheumatism, calcium crystal deposition arthritis, pseudogout, non-arthritic rheumatism, bursitis, tendosynovitis, epicondyle inflammation (tennis elbow), carpal tunnel syndrome, disorders by repetitive use (typing), mixed form of arthritis, neuropathic arthropathy, hemorrhagic arthritis, vascular peliosis, hypertrophic osteoarthropathy, multicentric reticulohistiocytosis, arthritis induced by specific diseases, blood pigmentation, sickle cell disease and other hemoglobin abnormality, hyperlipoproteinemia, dysgammaglobulinemia, hyperparathyroidism, acromegaly, familial Mediterranean fever, Bechet's disease, systemic autoimmune disease erythematosus, multiple sclerosis and Crohn's disease or diseases like relapsing polychondritis, chronic inflammatory bowel diseases (IBD) or the related diseases which require the administration to a mammal in a therapeutic effective dose of a compound expressed by Formula (I) in a sufficient dose to inhibit NADPH oxidase.

The term "liver diseases or disorders" include liver fibrosis, alcohol induced fibrosis, steatosis and non alcoholic steatohepatitis.

The term "arthritis" means acute rheumatic arthritis, chronic rheumatoid arthritis, chlamydial arthritis, chronic absorptive arthritis, chylous arthritis, arthritis based on bowel disease, filarial arthritis, gonorrheal arthritis, gouty arthritis, hemophilic arthritis, hypertrophic arthritis, juvenile chronic arthritis, Lyme arthritis, neonatal foal arthritis, nodular arthritis, ochronotic arthritis, psoriatic arthritis or suppurative arthritis, or the related diseases which require the administration to a mammal in a therapeutic effective dose of a compound expressed by Formula (I) in a sufficient dose to inhibit NADPH oxidase.

The term "pain" includes hyperalgesia associated with inflammatory pain.

The term "cancer" means carcinoma (e.g., fibrosarcoma, myxosarcoma, liposarcoma, chondrosarcoma, osteogenic sarcoma, chordoma, angiosarcoma, endothelium sarcoma, lymphangiosarcoma, lymphangioendothelioma, periosteoma, mesothelioma, Ewing's tumor, leiomyosarcoma, rhabdomyosarcoma, colon carcinoma, pancreatic cancer, breast cancer, ovarian cancer, renal cancer, prostatic carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, embryonal carcinoma, Wilms' tumor, cervical cancer, orchioncus, lung cancer, small-cell lung cancer, lung adenocarcinoma, bladder cancer or epithelial cancer) or the related diseases which require the administration to a mammal in a therapeutic effective dose of a compound expressed by the Formula (I) in a sufficient dose to inhibit NADPH oxidase.

The term "disease or disorders of the gastrointestinal system", includes gastric mucosa disorders ischemic bowel disease management, enteritis/colitis, cancer chemotherapy, or neutropenia.

The term "angiogenesis" includes sprouting angiogenesis, intussusceptive angiogenesis, vasculogenesis, arteriogenesis and lymphangiogenesis. Angiogenesis is the formation of new blood vessels from pre-existing capillaries or post-capillary venules and occurs in pathological conditions such as cancers, arthritis and inflammation. A large variety of tissues, or organs comprised of organized tissues, can support angiogenesis in disease conditions including skin, muscle, gut, connective tissue, joints, bones and the like tissue in which blood vessels can invade upon angiogenic stimuli. As used herein, the term "angiogenesis-dependent condition" is intended to mean a condition where the process of angiogenesis or vasculogenesis sustains or augments a pathological condition. Vasculogenesis results from the formation of new blood vessels arising from angioblasts which are endothelial cell precursors. Both processes result in new blood vessel formation and are included in the meaning of the term angiogenesis-dependent conditions. Similarly, the term "angiogenesis" as used herein is intended to include de novo formation of vessels such as those arising from vasculogenesis as well as those arising from branching and sprouting of existing vessels, capillaries and venules.

The term "angiogenesis inhibitory," means which is effective in the decrease in the extent, amount, or rate of neovascularization. Effecting a decrease in the extent, amount, or rate of endothelial cell proliferation or migration in the tissue is a specific example of inhibiting angiogenesis. Angiogenesis inhibitory activity is particularly useful in the treatment of any cancers as it targets tumor growth process and in the absence of neovascularization of tumor tissue, the tumor tissue does not obtain the required nutrients, slows in growth, ceases additional growth, regresses and ultimately becomes necrotic resulting in killing of the tumor. Further, an angiogenesis inhibitory activity is particularly useful in the treatment of any cancers as it is particularly effective against the formation of metastases because their formation also requires vascularization of a primary tumor so that the metastatic cancer cells can exit the primary tumor and their establishment in a secondary site requires neovascularization to support growth of the metastases.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions.

The term "subject" as used herein refers to mammals. For examples, mammals contemplated by the present invention include human, primates, domesticated animals such as cattle, sheep, pigs, horses and the like.

The term "inhibitor" used in the context of the invention is defined as a molecule that inhibits completely or partially the activity of NADPH oxidase and/or inhibit or reduce the generation of reactive oxygen species (ROS).

Compounds According to the Invention

In one embodiment, the invention provides a pyrazoline dione derivative according to Formula (I):

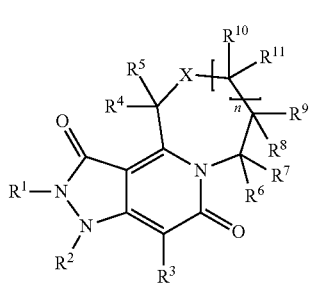

(I)

wherein $R^1$ is selected from H; optionally substituted alkoxycarbonyl; optionally substituted $C_1$-$C_6$ alkyl; optionally substituted $C_2$-$C_6$ alkenyl; optionally substituted $C_2$-$C_6$ alkynyl; optionally substituted alkoxy; optionally substituted alkoxy $C_1$-$C_6$ alkyl; optionally substituted aminoalkyl; optionally substituted acyl; optionally substituted aryl such as optionally substituted phenyl (e.g. 2-chlorophenyl, 2-methoxyphenyl); optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; $R^2$ is selected from H; optionally substituted alkoxycarbonyl; optionally substituted acyl; optionally substituted acyl $C_1$-$C_6$ alkyl; optionally substituted $C_1$-$C_6$ alkyl; optionally substituted $C_2$-$C_6$ alkenyl; optionally substituted $C_2$-$C_6$ alkynyl; optionally substituted aryl; optionally substituted heteroaryl; optionally substituted $C_3$-$C_8$-cycloalkyl; optionally substituted heterocycloalkyl; optionally substituted $C_3$-$C_8$-cycloalkyl $C_1$-$C_6$ alkyl; optionally substituted heterocycloalkyl $C_1$-$C_6$ alkyl; optionally substituted aryl $C_1$-$C_6$ alkyl and optionally substituted heteroaryl $C_1$-$C_6$ alkyl; $R^3$ is selected is selected from H; optionally substituted alkoxycarbonyl; optionally substituted acyl; optionally substituted $C_1$-$C_6$ alkyl; optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; $R^4$, $R^5$, $R^6$, $R^7$, $R^8$ and $R^9$ are independently selected from H; halogen; nitro; optionally substituted $C_1$-$C_6$ alkyl; optionally substituted $C_2$-$C_6$ alkenyl; optionally substituted $C_2$-$C_6$ alkynyl; optionally substituted amino; optionally substituted aminoalkyl; optionally substituted alkoxy; and optionally substituted alkoxy $C_1$-$C_6$ alkyl; $R^{10}$ is selected from H and optionally substituted $C_1$-$C_6$ alkyl; $R^{11}$ is selected from H; optionally substituted alkoxycarbonyl; optionally substituted acyl; optionally substituted $C_1$-$C_6$ alkyl; optionally substituted $C_2$-$C_6$ alkenyl; optionally substituted $C_2$-$C_6$ alkynyl; optionally substituted alkoxy; optionally substituted alkoxy $C_1$-$C_6$ alkyl; optionally substituted aminoalkyl; optionally substituted acyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; $R^{12}$ is selected from H; —Z—$NR^{13}R^{14}$; —$CHR^{17}R^{18}$; optionally substituted alkoxycarbonyl such as optionally substituted carboxylate (e.g. tert-butyl carboxylate); optionally substituted acyl; optionally substituted $C_1$-$C_6$ alkyl; optionally substituted $C_2$-$C_6$ alkenyl; optionally substituted $C_2$-$C_6$ alkynyl; optionally substituted alkoxy; optionally substituted alkoxy $C_1$-$C_6$ alkyl; optionally substituted aminoalkyl; optionally substituted acyl; optionally substituted aryl; optionally substituted $C_1$-$C_6$ alkyl aryl; optionally substituted aryl $C_1$-$C_6$ alkyl such as optionally substituted phenyl $C_1$-$C_6$ alkyl such as optionally substituted phenyl methyl (e.g. benzyl, 2-chlorobenzyl, 3-methoxybenzyl, 3-chlorobenzyl, 4-chlorobenzyl, 2-methoxybenzyl; optionally substituted heteroaryl; optionally substituted $C_1$-$C_6$ alkyl heteroaryl; optionally substituted heteroaryl $C_1$-$C_6$ alkyl such as optionally substituted pyridine $C_1$-$C_6$ alkyl (e.g. optionally substituted pyridine methyl such as pyridine-2-ylmethyl, pyridine-3-ylmethyl) or optionally substituted furanyl $C_1$-$C_6$ alkyl (e.g. optionally substituted furan methyl such as furan-3-ylmethyl) or optionally substituted pyrazolyl $C_1$-$C_6$ alkyl (e.g. optionally substituted pyrazolyl methyl such as 1-methyl-1H-pyrazol-3-yl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; $R^{13}$, $R^{14}$, $R^{17}$ and $R^{18}$ are independently selected from H; optionally substituted $C_1$-$C_6$ alkyl; optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; X is selected from O, $NR^{12}$, S, S=O and $S(O)_2$; Z is selected from C(O); C(S) and $SO_2$; n is an integer selected from 0 and 1; as well as pharmaceutically acceptable salts and pharmaceutically active derivative thereof.

Compositions

The invention provides pharmaceutical or therapeutic agents as compositions and methods for treating a patient, preferably a mammalian patient, and most preferably a human patient who is suffering from a medical disorder, and in particular a disorder mediated by NADPH oxidase, such as a cardiovascular disorder or disease, a respiratory disorder or disease, a disease or disorder affecting the metabolism, a skin disorder, a bone disorder, a neuroinflammatory disorder, a neurodegenerative disorder, a kidney disease, a reproduction disorder, a disease or disorder affecting the eye and/or the lens, a condition affecting the inner ear, an inflammatory disorder or disease, a liver disease, pain, a cancer, angiogenesis, angiogenesis-dependent conditions and/or a disease or disorders of the gastrointestinal system.

Pharmaceutical compositions of the invention can contain one or more pyrazoline dione derivative in any form described herein. Compositions of this invention may further comprise one or more pharmaceutically acceptable additional ingredient(s), such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. Compositions according to the invention are preferably injectable.

Compositions of this invention may also be liquid formulations, including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives, including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in Part 5 of *Remington's Pharmaceutical Sciences*, 21$^{st}$ *Edition*, 2005, University of the Sciences in Philadelphia, Lippincott Williams & Wilkins, which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration, including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the stratum corneum, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the stratum corneum. The compounds of this invention can also be administered in sustained release forms or from sustained release drug delivery systems. A description of representative sustained release materials can also be found in the incorporated materials in *Remington's Pharmaceutical Sciences*.

Mode of Administration

Compositions of this invention may be administered in any manner, including, but not limited to, orally, parenterally, sublingually, transdermally, rectally, transmucosally, topically, via inhalation, via buccal or intranasal administration, or combinations thereof. Parenteral administration includes, but is not limited to, intravenous, intra-arterial, intra-peritoneal, subcutaneous, intramuscular, intra-thecal, and intra-articular. The compositions of this invention may also be administered in the form of an implant, which allows slow release of the compositions as well as a slow controlled i.v. infusion. In a preferred embodiment, pyrazoline dione derivatives according to the invention are administered intravenously or subcutaneously.

This invention is further illustrated by the following examples that are not intended to limit the scope of the invention in any way.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Combination

According to one embodiment of the invention, the compounds according to the invention and pharmaceutical formulations thereof can be administered alone or in combination with a co-agent useful in the treatment of cancer, such as substances used in conventional chemotherapy directed against solid tumors and for control of establishment of metastases or substances used in hormonotherapy or any other molecule that act by triggering programmed cell death e.g. for example a co-agent selected from the category of drugs that stop the synthesis of pre DNA molecule building blocks such as methotrexate (Abitrexate®), fluorouracil (Adrucil®), hydroxyurea (Hydrea®), and mercaptopurine (Purinethol®). e.g. for example a co-agent selected from the category of drugs that directly damage the DNA in the nucleus of the cell such as cisplatin (Platinol®) and antibiotics—daunorubicin (Cerubidine®), doxorubicin (Adriamycin®), and etoposide (VePesid®). e.g. for example a co-agent selected from the category of drugs that effect the synthesis or breakdown of the mitotic spindles such as Vinblastine (Velban®), Vincristine (Oncovin®) and Pacitaxel (Taxol®).

According to another embodiment of the invention, the compounds according to the invention and pharmaceutical formulations thereof can be administered in combination with agents targeting cell-surface proteins such as gene transfer of cytokine receptor chain and receptor-targeted cytotoxin administration According to another embodiment of the invention, the compounds according to the invention and pharmaceutical formulations thereof can be administered in combination with radiation therapy.

The invention encompasses the administration of a compound according to the invention or of a pharmaceutical formulation thereof, wherein the compound according to the invention or the pharmaceutical formulation thereof is administered to an individual prior to, simultaneously or sequentially with other therapeutic regimens or co-agents useful in the treatment of cancers (e.g. multiple drug regimens), in a therapeutically effective amount. Compounds according to the invention or the pharmaceutical formulations thereof that are administered simultaneously with said co-agents can be administered in the same or different composition(s) and by the same or different route(s) of administration.

In another particular embodiment, the compounds and methods of the invention are contemplated for use in the treatment of cancers wherein the administration of a compound according to the invention is typically conducted during or after chemotherapy, hormonotherapy or radiotherapy.

In another particular embodiment, the compounds and methods of the invention are contemplated for use in the treatment of cancers wherein the administration of a compound according to the invention is typically conducted after a regimen of chemotherapy, hormonotherapy or radiotherapy at times where the tumor tissue will be responding to the toxic assault by inducing angiogenesis to recover by the provision of a blood supply and nutrients to the tumor tissue.

In another embodiment, the administration of a compound according to the invention is performed after surgery where solid tumors have been removed as a prophylaxis against metastases.

Patients

In an embodiment, patients according to the invention are patients suffering from a cardiovascular disorder or disease.

In another embodiment, patients according to the invention are patients suffering from a respiratory disorder or disease.

In another embodiment, patients according to the invention are patients suffering from a disease or disorder affecting the metabolism.

In another embodiment, patients according to the invention are patients suffering from a skin disorder.

In another embodiment, patients according to the invention are patients suffering from a bone disorder.

In another embodiment, patients according to the invention are patients suffering from a neuroinflammatory disorder and/or a neurodegenerative disorder.

In another embodiment, patients according to the invention are patients suffering from a kidney disease.

In another embodiment, patients according to the invention are patients suffering from a reproduction disorder.

In another embodiment, patients according to the invention are patients suffering from a disease or disorder affecting the eye and/or the lens and/or a condition affecting the inner ear.

In another embodiment, patients according to the invention are patients suffering from an inflammatory disorder or disease.

In another embodiment, patients according to the invention are patients suffering from a liver disease.

In another embodiment, patients according to the invention are patients suffering from pain, such as inflammatory pain.

In another embodiment, patients according to the invention are patients suffering from a cancer.

In another embodiment, patients according to the invention are suffering from angiogenesis or an angiogenesis-dependent condition.

In another embodiment, patients according to the invention are patients suffering from allergic disorders.

In another embodiment, patients according to the invention are patients suffering from traumatisms.

In another embodiment, patients according to the invention are patients suffering from septic, hemorrhagic and anaphylactic shock.

In another embodiment, patients according to the invention are patients suffering from a disease or disorders of the gastrointestinal system.

Use According to the Invention

In another embodiment, the invention provides a pyrazoline dione derivative according to Formula (I); as well as pharmaceutically acceptable salts and pharmaceutically active derivative thereof for use as a medicament.

In a further embodiment, the invention provides a pyrazoline dione derivative according to the invention wherein $R^1$ is selected from optionally substituted aryl and optionally substituted heteroaryl; $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, X and n are as defined in the detailed description.

In another further embodiment, the invention provides a pyrazoline dione derivative according to the invention wherein $R^2$ is H; $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, X and n are as defined in the detailed description.

In another further embodiment, the invention provides a pyrazoline dione derivative according to the invention wherein $R^3$ is H; $R^1$, $R^2$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, X and n are as defined in the detailed description.

In another further embodiment, the invention provides a pyrazoline dione derivative according to the invention wherein $R^4$ is H; $R^1$, $R^2$, $R^3$, $R^5$, $R^6$, $R^7$, $R^8$, $R^9$, $R^{10}$, $R^{11}$, $R^{12}$, $R^{13}$, $R^{14}$, $R^{17}$, $R^{18}$, X and n are as defined in the detailed description.

In another further embodiment, the invention provides a pyrazoline dione derivative according to the invention wherein $R^4$ and $R^5$ are H; $R^1$, $R^2$, $R^3$, $R^6$, $R^7$, $R^8$, $R^9$, $R^{10}$, $R^{11}$, $R^{12}$, $R^{13}$, $R^{14}$, $R^{17}$, $R^{18}$, X and n are as defined in the detailed description.

In another further embodiment, the invention provides a pyrazoline dione derivative according to the invention wherein $R^4$, $R^5$, $R^6$, $R^7$, $R^8$ and $R^9$ are H; $R^1$, $R^2$, $R^3$, $R^{10}$, $R^{11}$, $R^{12}$, $R^{13}$, $R^{14}$, $R^{17}$, $R^{18}$, X and n are as defined in the detailed description.

In another further embodiment, the invention provides a pyrazoline dione derivative according to the invention wherein $R^{10}$ is H; $R^1$, $R^2$, $R^3$, $R^4$, $R^5$, $R^6$, $R^7$, $R^8$, $R^9$, $R^{11}$, $R^{12}$, $R^{13}$, $R^{14}$, $R^{17}$, $R^{18}$, X and n are as defined in the detailed description.

In another further embodiment, the invention provides a pyrazoline dione derivative according to the invention wherein $R^{11}$ is H; $R^1$, $R^2$, $R^3$, $R^4$, $R^5$, $R^6$, $R^7$, $R^8$, $R^9$, $R^{10}$, $R^{12}$, $R^{13}$, $R^{14}$, $R^{17}$, $R^{18}$, X and n are as defined in the detailed description.

In another further embodiment, the invention provides a pyrazoline dione derivative according to the invention wherein $R^{12}$ is H; $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{17}$, $R^{18}$, X and n are as defined in the detailed description.

In another further embodiment, the invention provides a pyrazoline dione derivative according to the invention wherein $R^{12}$ is selected from optionally substituted aryl $C_1$-$C_6$ and optionally substituted heteroaryl $C_1$-$C_6$ alkyl; $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{17}$, $R^{18}$, X and n are as defined in the detailed description.

In another further embodiment, the invention provides a pyrazoline dione derivative according to the invention wherein $R^{12}$ is optionally substituted alkoxycarbonyl; $R^1$, $R^2$, $R^3$, $R^4$, $R^5$, $R^6$, $R^7$, $R^8$, $R^9$, $R^{10}$, $R^{11}$, $R^{13}$, $R^{14}$, $R^{17}$, $R^{18}$, X and n are as defined in the detailed description.

In another further embodiment, the invention provides a pyrazoline dione derivative according to the invention wherein X is O; $R^1$, $R^2$, $R^3$, $R^4$, $R^5$, $R^6$, $R^7$, $R^8$, $R^9$, $R^{10}$, $R^{11}$ and n are as defined in the detailed description.

In another further embodiment, the invention provides a pyrazoline dione derivative according to the invention wherein X is $NR^{12}$; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, and n are as defined in the detailed description.

In another further embodiment, the invention provides a pyrazoline dione derivative according to the invention wherein n is 0; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, and X are as defined in the detailed description.

In another further embodiment, the invention provides a pyrazoline dione derivative according to the invention wherein n is 1; $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, and X are as defined in the detailed description.

In another further embodiment, the invention provides a pyrazoline dione derivative according to the invention wherein $R^2$, $R^3$, $R^4$, $R^5$, $R^6$, $R^7$, $R^8$, $R^9$, $R^{19}$ and $R^{11}$ are H; $R^1$, $R^{12}$, $R^{13}$, $R^{14}$, $R^{17}$, $R^{18}$, X and n are as defined in the detailed description.

In another further embodiment, the invention provides a pyrazoline dione derivative according to the invention wherein $R^2$, $R^3$, $R^4$, $R^5$, $R^6$, $R^7$, $R^8$, $R^9$, $R^{10}$, $R^{11}$ and $R^{17}$ are H; $R^{12}$ is —$CHR^{17}R^{18}$; X is $NR^{12}$; $R^1$, $R^{18}$ and n are as defined in the detailed description.

In another embodiment, the invention provides a use of a pyrazoline dione derivative according to Formula (I) wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, X and n are as defined in the detailed description, as well as pharmaceutically acceptable salts and pharmaceutically active derivative thereof for the preparation of a pharmaceutical composition for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, disorders of the gastrointestinal system, angiogenesis, angiogenesis-dependent conditions and other diseases and disorders associated with Nicotinamide adenine dinucleotide phosphate oxidase (NADPH Oxidase).

In another embodiment, the invention provides a pyrazoline dione derivative according to Formula (I) wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, X and n are as defined in the detailed description, as well as pharmaceutically acceptable salts and pharmaceutically active derivative thereof for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, disorders of the gastrointestinal system, angiogenesis, angiogenesis-dependent conditions and other diseases and disorders associated with Nicotinamide adenine dinucleotide phosphate oxidase (NADPH Oxidase).

Compounds of the present invention include in particular those selected from the following group:

2-(2-chlorophenyl)-10-(pyridin-2-ylmethyl)-2,3,8,9,10,11-hexahydro-1H-pyrazolo[4',3':3,4]pyrido[1,2-a][1,4]diazepine-1,5(7H)-dione;

10-benzyl-2-(2-methoxyphenyl)-2,3,8,9,10,11-hexahydro-1H-pyrazolo[4',3':3,4]pyrido[1,2-a][1,4]diazepine-1,5(7H)-dione;

10-benzyl-2-(2-chlorophenyl)-2,3,8,9,10,11-hexahydro-1H-pyrazolo[4',3':3,4]pyrido[1,2-a][1,4]diazepine-1,5(7H)-dione;

10-(2-chlorobenzyl)-2-(2-chlorophenyl)-2,3,8,9,10,11-hexahydro-1H-pyrazolo[4',3':3,4]pyrido[1,2-a][1,4]diazepine-1,5(7H)-dione;

2-(2-chlorophenyl)-10-(3-methoxybenzyl)-2,3,8,9,10,11-hexahydro-1H-pyrazolo[4',3':3,4]pyrido[1,2-a][1,4]diazepine-1,5(7H)-dione;

10-(3-chlorobenzyl)-2-(2-chlorophenyl)-2,3,8,9,10,11-hexahydro-1H-pyrazolo[4',3':3,4]pyrido[1,2-a][1,4]diazepine-1,5(7H)-dione;

2-(2-chlorophenyl)-2,3,8,9,10,11-hexahydro-1H-pyrazolo[4',3':3,4]pyrido[1,2-a][1,4]diazepine-1,5(7H)-dione;

tert-butyl 2-(2-chlorophenyl)-1,5-dioxo-2,3,5,8,9,11-hexahydro-1H-pyrazolo[4',3':3,4]pyrido[1,2-a][1,4]diazepine-10(7H)-carboxylate;

10-(4-chlorobenzyl)-2-(2-chlorophenyl)-2,3,8,9,10,11-hexahydro-1H-pyrazolo[4',3':3,4]pyrido[1,2-a][1,4]diazepine-1,5(7H)-dione;

2-(2-chlorophenyl)-10-(2-methoxybenzyl)-2,3,8,9,10,11-hexahydro-1H-pyrazolo[4',3':3,4]pyrido[1,2-a][1,4]diazepine-1,5(7H)-dione;

2-(2-chlorophenyl)-10-(4-methoxybenzyl)-2,3,8,9,10,11-hexahydro-1H-pyrazolo[4',3':3,4]pyrido[1,2-a][1,4]diazepine-1,5(7H)-dione;

2-(2-chlorophenyl)-10-(furan-3-ylmethyl)-2,3,8,9,10,11-hexahydro-1H-pyrazolo[4',3':3,4]pyrido[1,2-a][1,4]diazepine-1,5(7H)-dione;

9-benzyl-2-(2-chlorophenyl)-2,3,7,8,9,10-hexahydropyrazolo[4',3':3,4]pyrido[1,2-a]pyrazine-1,5-dione;

2-(2-chlorophenyl)-2,3,7,8-tetrahydro-1H-pyrazolo[4',3':3,4]pyrido[2,1-c][1,4]oxazine-1,5(10H)-dione;

2-(2-methoxyphenyl)-10-(pyridin-2-ylmethyl)-2,3,8,9,10,11-hexahydro-1H-pyrazolo[4',3':3,4]pyrido[1,2-a][1,4]diazepine-1,5(7H)-dione;

10-(3-methoxybenzyl)-2-(2-methoxyphenyl)-2,3,8,9,10,11-hexahydro-1H-pyrazolo[4',3':3,4]pyrido[1,2-a][1,4]diazepine-1,5(7H)-dione;

2-(2-chlorophenyl)-10-[(1-methyl-1H-pyrazol-3-yl)methyl]-2,3,8,9,10,11-hexahydro-1H-pyrazolo[4',3':3,4]pyrido[1,2-a][1,4]diazepine-1,5(7H)-dione; and 2-(2-chlorophenyl)-10-(pyridin-3-ylmethyl)-2,3,8,9,10,11-hexahydro-1H-pyrazolo[4',3':3,4]pyrido[1,2-a][1,4]diazepine-1,5(7H)-dione.

In another embodiment, the invention provides an intermediate of Formula (II):

(II)

wherein $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{17}$, $R^{18}$, X and n are as defined in the detailed description; $R^{15}$ is an optionally substituted $C_1$-$C_6$ alkyl such as methyl, ethyl, propyl, isopropyl or butyl.

In a further embodiment, the invention provides an intermediate of Formula (II) according to the invention, wherein the intermediate is selected from the group consisting of:
methyl [(4Z)-4-(4-benzyl-1,4-diazepan-2-ylidene)-1-(2-chlorophenyl)-5-oxo-4,5-dihydro-1H-pyrazol-3-yl]acetate; and methyl [(4Z)-4-(4-benzyl-1,4-diazepan-2-ylidene)-1-(2-methoxyphenyl)-5-oxo-4,5-dihydro-1H-pyrazol-3-yl]acetate.

In another embodiment, the invention provides a process for the preparation of an intermediate according to Formula (II), comprising the step of reacting a compound of Formula (V) with an amine of Formula (IV):

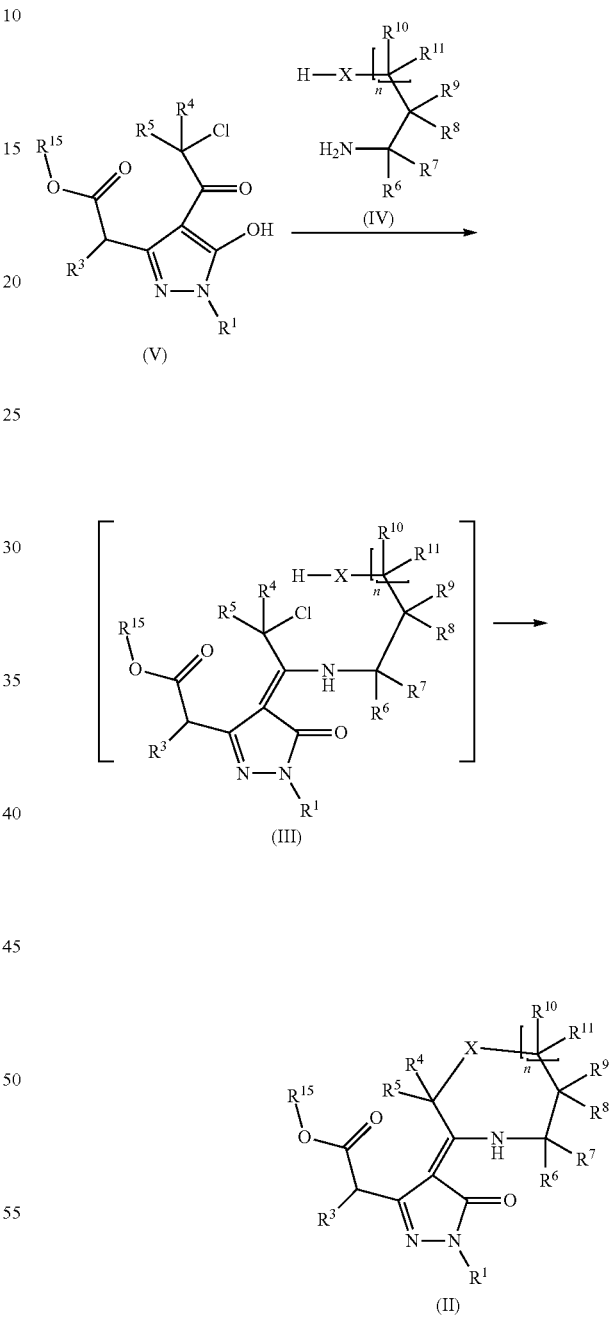

wherein $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{17}$, $R^{18}$, X and n are as defined in the detailed description.

In another embodiment, the invention provides a process for the preparation of a compound according to Formula (I), comprising the step of cyclizing a compound of Formula (II) in presence of a base:

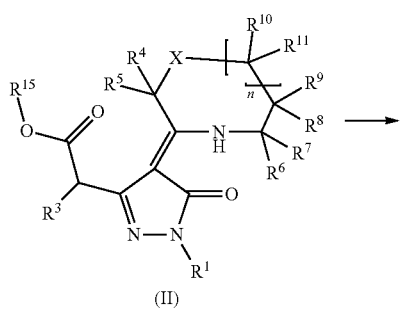

(II)

wherein $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{17}$, $R^{18}$, X and n are as defined in the detailed description; $R^2$ is H.

In another embodiment, the invention provides a process for the preparation of a compound according to Formula (I), comprising reacting a compound of Formula (Ia) with an alkylating agent or a coupling agent in presence of a base:

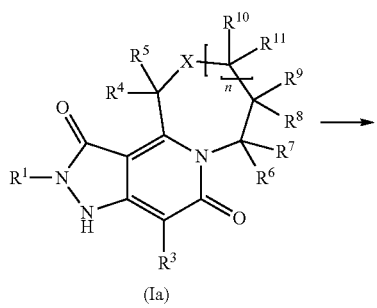

(Ia)

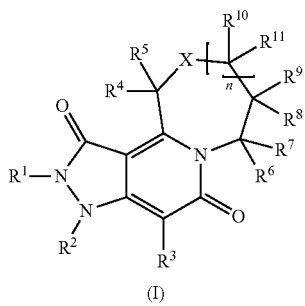

(I)

wherein $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, X and n are as defined in the detailed description; $R^2$ is as described in the description but is other than H.

In another embodiment, the invention provides a method for treating a patient suffering from a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers allergic disorders, traumatisms, septic, hemorrhagic and anaphylactic shock, disorders of the gastrointestinal system, angiogenesis, angiogenesis-dependent conditions and other diseases and disorders associated with Nicotinamide adenine dinucleotide phosphate oxidase (NADPH Oxidase). The method comprises administering a compound according to Formula (I) in a patient in need thereof.

In another embodiment, the invention provides a method for inhibiting angiogenesis in a patient in need thereof, wherein the method comprises administering an angiogenesis inhibiting dose of a compound of Formula (I) in a patient in need thereof.

In another embodiment, the invention provides a method of inhibiting tumor neovascularization by inhibiting tumor angiogenesis according to the present methods. Similarly, the invention provides a method for inhibiting tumor growth by practicing the angiogenesis-inhibiting methods.

In a particular embodiment, the compounds and methods of the invention are contemplated for use in treatment of a tumor tissue of a patient with a tumor, solid tumor, a metastasis, a cancer, a melanoma, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present compounds and methods include, but are not limited to, tumors of the skin, melanoma, lung, pancreas, breast, colon, laryngeal, ovarian, prostate, colorectal, head, neck, testicular, lymphoid, marrow, bone, sarcoma, renal, sweat gland, and the like tissues. Further examples of cancers treated are glioblastomas.

In another particular embodiment, the compounds and methods of the invention are contemplated for use in treatment of an inflamed tissue and the angiogenesis to be inhibited is inflamed tissue angiogenesis where there is neovascularization of inflamed tissue. In this case, the compound and method according to the invention contemplate the inhibition of angiogenesis in arthritic tissues, such as in a patient with chronic articular rheumatism, in immune or non-immune inflamed tissues, in psoriatic tissue and the like.

In embodiments, the invention contemplates inhibition of angiogenesis in a tissue. The extent of angiogenesis in a tissue, and therefore the extent of inhibition achieved by the present methods, can be evaluated by a variety of methods, such as are described herein.

In another embodiment, the invention provides a pharmaceutical composition containing at least one derivative pyrazoline dione according to Formula (I) and a pharmaceutically acceptable carrier, diluent or excipient thereof.

The compounds of invention have been named according the IUPAC standards used in the program ACD/Name (product version 10.01).

Compounds according to the present invention comprise a compound according to Formula (I), its tautomers, its geometrical isomers, its optically active forms as enantiomers, diastereomers and its racemate forms, as well as pharmaceutically acceptable salts thereof. The derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention having been described, the following examples are presented by way of illustration, and not limitation.

Synthesis of Compounds of the Invention:

The novel derivatives according to Formula (I) can be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

A general synthetic approach for obtaining compounds of Formula (I) is depicted in Scheme 1 below. Pyrazolo pyridine derivatives according to Formula (I), whereby the substituents $R^1, R^2, R^3, R^4, R^5, R^6, R^7, R^8, R^9, R^{10}, R^{11}, R^{12}, R^{13}, R^{14}, R^{17}, R^{18}$, X and n are as above defined, may be prepared in four to five chemical steps, from custom made or commercially available substituted hydrazine derivatives according to Formula (VIII), acetone dicarboxylate derivatives according to Formula (IX), primary amine derivatives according to Formula (IV), and trialkyl ortho ester derivative according to Formula (VI), following the synthetic pathway as outlined in Scheme 1 below. In a more specific method, a hydrazine derivative according to Formula (VIII) wherein $R^1$ is defined as above is reacted with an acetone dicarboxylate derivative according to Formula (IX) wherein $R^3$ and $R^{15}$ are as defined below, in neutral and under refluxing conditions in a suitable solvents like benzene, toluene or other unreactive solvents over time depending of the intrinsic reactivity of compounds according to Formula (VIII) to give the corresponding 4-substituted 2-hydroxyl pyrazole derivatives according to Formula (VII).

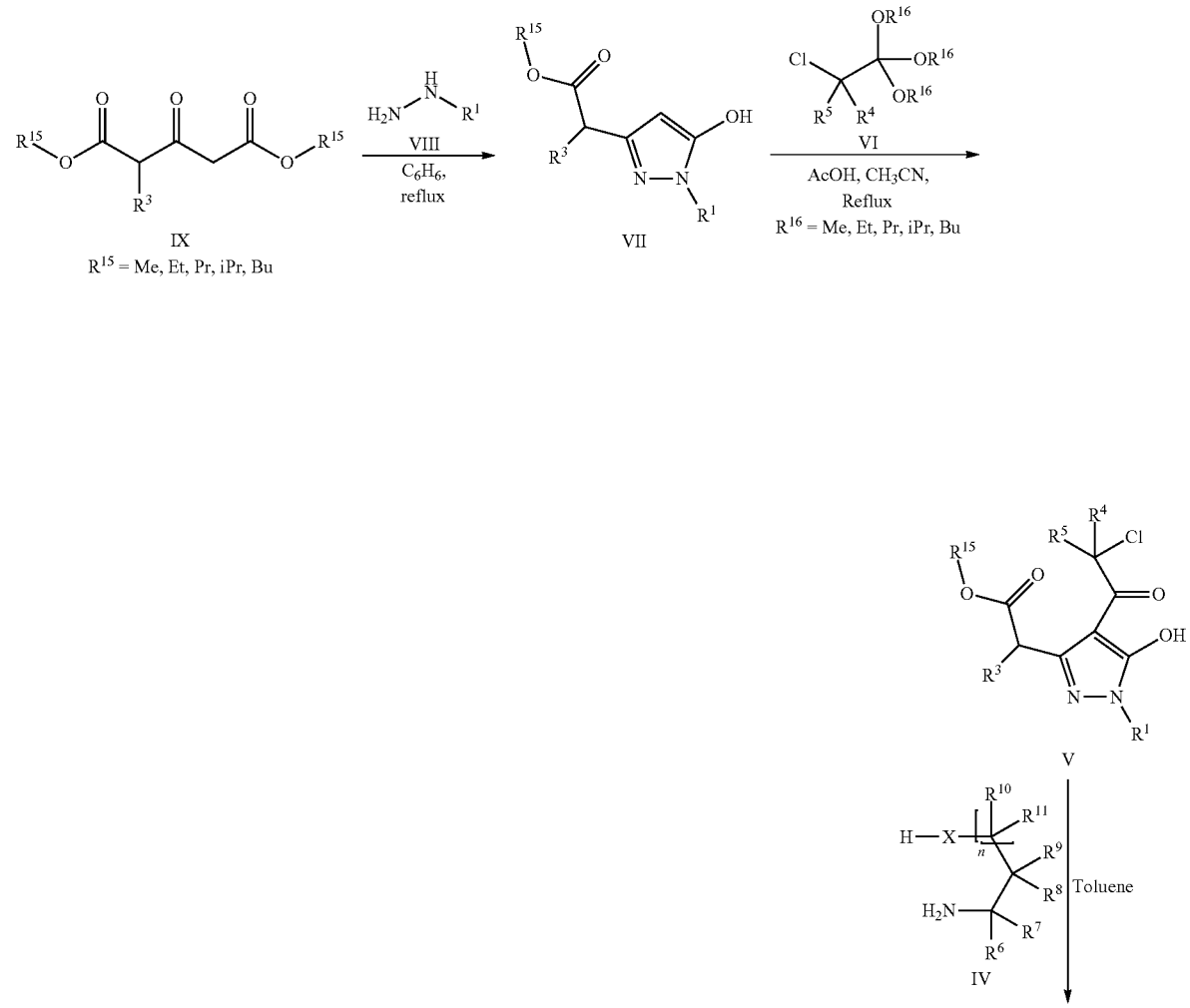

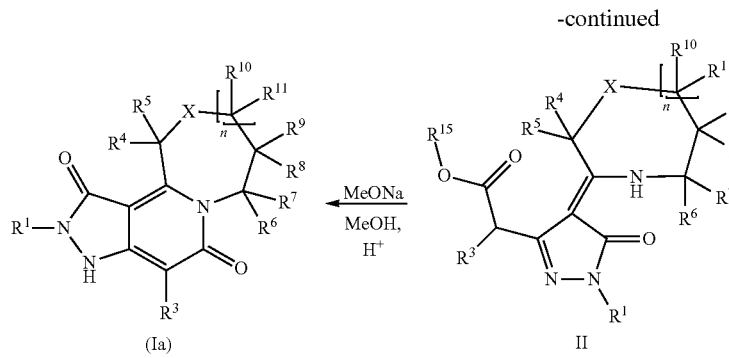
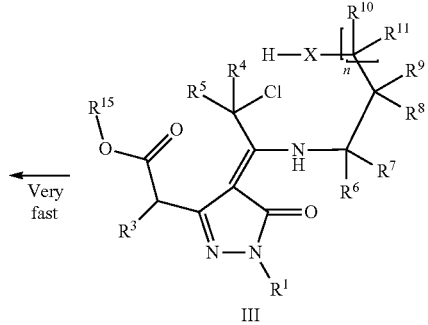

The intermediate compounds according to Formula (VII) are further reacted with trialkyl ortho ester derivative according to Formula (VI) wherein $R^4$, $R^5$ and $R^{16}$ are defined as above, to allow the formation of an intermediate of Formula (V) in presence of acetic acid and under refluxing conditions. Intermediate compounds of Formula (V) are further treated with primary amine derivatives according to Formula (IV) wherein $R^6$, $R^7$, $R^8$, $R^9$, $R^{10}$, $R^{11}$, X, and n are defined as above, in solvents such as acetonitrile at temperature below zero degree to room temperature, to obtain the intermediate compounds of Formula (III). Intermediate compounds of Formula (III) is usually not isolated and give spontaneously intermediate according to Formula (II) in situ in the same reaction conditions or sometimes required heating, wherein $R^1$, $R^3$, $R^4$, $R^5$, $R^6$, $R^7$, $R^8$, $R^9$, $R^{10}$, $R^{11}$, $R^{15}$, X and n are defined as above.

The pyrazolo derivatives according to Formula (Ia), i.e. of Formula (I) wherein $R^2$ is H, are isolated after cyclisation of intermediate compounds of Formula (II), preferably in protic solvents in presence of base such as sodium methanolate, sodium isopropanolate or the like, using standard refluxing conditions well known to the person skilled in the art as shown in Scheme 1. This reaction may be performed in solvents like methanol, ethanol, isopropanol or other unreactive solvents at room temperature over time depending of the intrinsic reactivity of compounds according to Formula (II), but usually requires traditional thermal heating or microwave methods, using standard conditions well known to the person skilled in the art as shown in Scheme 1 above.

In a subsequent step, the pyrazolo pyridine derivatives of Formula (Ia) were treated with an alkylating agent of Formula $R^2W$ such as alkyl chlorides, bromides, iodides or mesylates, wherein $R^2$ and W are as defined above, in presence of a suitable base, e.g. Triethylamine, sodium hydride or potassium carbonate as a base in a suitable solvent, e.g. N,N-dimethylformamide or tetrahydrofuran, by traditional thermic method or using microwave technology. Alternatively, the pyrazolo pyridine derivatives of Formula (Ia) were treated with anhydrides, acyl chlorides, or carboxylic acids, wherein $R^2$ is defined as above, in presence of a coupling agent such as N,N'-Dicyclohexylcarbodiimide in presence of a suitable base, e.g. Triethylamine, in a suitable solvent, e.g. N,N-dimethylformamide or tetrahydrofuran, dichloromethane by traditional thermic method or using microwave technology. Following these processes the pyrazolo pyridine derivatives according to Formula (Ib) are isolated, using standard conditions well known to the person skilled in the art as shown in Scheme 2.

Scheme 2

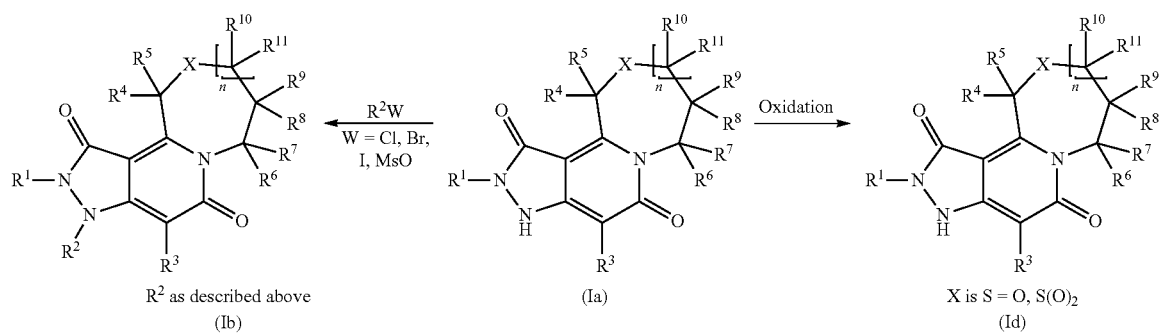

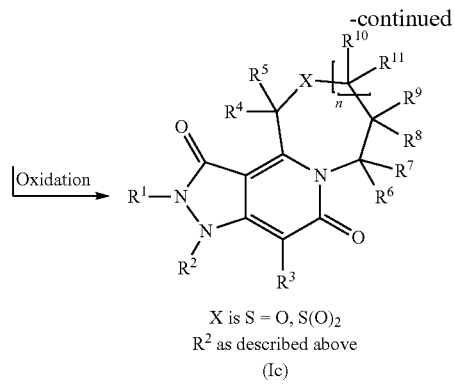

X is S = O, S(O)₂
R² as described above
(Ic)

In another subsequent step, the pyrazolo pyridine derivatives of Formula (Ia or Ib) were treated with an oxidizing agent such as e.g. m-Chloroperbenzoic acid or oxygen in presence of meso-Tetraphenylporphine by traditional thermic method or using photochemistry technology. This reaction may be performed in solvents like tetrahydrofurane or dichloromethane or other unreactive solvents at room temperature over time depending of the intrinsic reactivity of compounds according to Formula (Ia or Ib). Following this process the pyrazolo pyridine derivatives according to Formula (Ic or Id) are isolated using standard conditions well known to the person skilled in the art as shown in Scheme 2 above.

Primary amine derivatives according to Formula (IV') wherein X are NCHR¹⁷R¹⁸ and substituents R⁶, R⁷, R⁸, R⁹, R¹⁰, R¹¹, R¹⁷, R¹⁸ and n are as above defined, may be prepared from intermediates of Formulae (XI) or (X) in one to two chemical steps, from custom made or commercially available substituted amine derivatives according to Formula (X), and aldehyde or ketone derivatives according to Formula (XII), following the synthetic pathway as outlined in Scheme 3 below.

Scheme 3

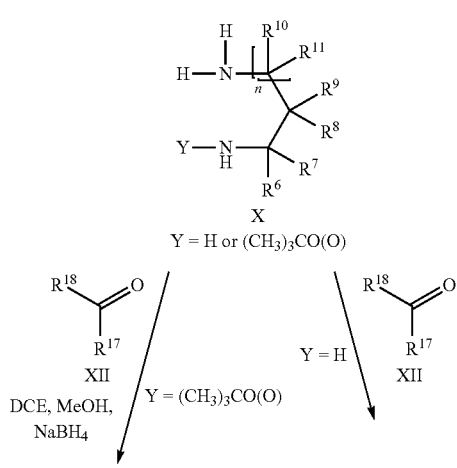

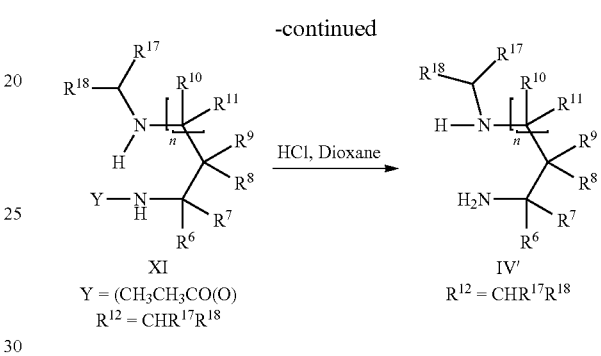

Y = (CH₃CH₃CO(O))
R¹² = CHR¹⁷R¹⁸

R¹² = CHR¹⁷R¹⁸

In a more specific method, a substituted amine derivative according to Formula (X), wherein R⁶, R⁷, R⁸, R⁹, R¹⁰, R¹¹ and n are defined as above is reacted, in presence of a reductive agent such as sodium orohydride, with an aldehyde or a ketone derivative according to Formula (XII) wherein R¹⁷, R¹⁸ is defined as above, in a suitable solvent like dichloroethane, dichloromethane and methanol, or other unreactive solvents over time depending of the intrinsic reactivity of compounds according to Formula (XII) to give the corresponding amine derivatives according to Formula (XI) or Formula (IV'), i.e. of Formula (IV) wherein X is NCHR¹⁷R¹⁸. The intermediate compounds according to Formula (XI) are further treated with hydrochloride acid in a suitable solvent such as dioxane, to obtain the primary amine derivatives according to Formula (IV'), wherein R⁶, R⁷, R⁸, R⁹, R¹⁰, R¹¹, R¹⁷, R¹⁸ and n are defined as above, using standard conditions well known to the person skilled in the art as shown in Scheme 3.

The following abbreviations refer respectively to the definitions below:

Å (Angstrom), Ac₂O (Acetic anhydride), eq. (equivalent), min (minute), h (hour), g (gram), MHz (Megahertz), mL (milliliter), mm (millimeter), mmol (millimole), mM (millimolar), ng (nanogram), nm (nanometer), rt (room temperature), α-SMA (alpha smooth muscle actin), BLM (Bleomycin), BSA (Bovine serum albumin), DCE (dichloroethane), DCF (2,7-dichlorodihydrofluorescein), DCM (dichloromethane), DEPC (diethyl pyrocarbonate), DIPEA (di-isopropyl ethylamine), DMSO (Dimethyl Sulfoxide), DMF (N,N-Dimethylformamide), DAPI (4,6 Diamidino-2-phenylindole), DPI (Diphenyl-iodonium), cHex (Cyclohexane), EDTA (ethylenediaminetetraacetic acid), EGF (Epidermal Growth Factor), EtOAc (Ethyl acetate), FC (Flash Chromatography on silica gel), GAPDH (Glyceraldehyde 3 phosphate dehydrogenase), HBSS (Hank's Buffered Salt Solution), HPLC (High performance liquid chromatography), H₂DCF-DA (2',7'-dichlorodihydrofluorescein diacetate), MEM (2-methoxyethoxymethyl), MS (Mass Spectrometry), MOPS (3-(N-morpholino) propanesulfonic acid), NaBH4 (Sodium borohydride), NADPH (Nicotinamide adenine dinucleotide diphosphate reduced form), NBT (Nitroblue tetrazolium), NMR (Nuclear magnetic resonance), PBS (Phosphate Buffered Saline), PetEther (Petroleum ether), ROS (Reactive oxygen species), RIPA (Radioimmunoprecipitation buffer), SDS (sodium dodecyl sulfate), SOD (Superoxide dismutase), SPA (Scintillation proximity assay), tBuOK (Potassium tert-butoxide), TEA (Triethyl amine), TFA (Trifluoroacetic acid), TGF-β (Tumor Growth Factor beta), THF (Tetrahydrofuran), TLC (Thin layer chromatography), TRIS (trishydroxymethylaminomethane), UV (Ultraviolet).

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in *"Protecting Groups"*, Georg Thieme Verlag Stuttgart, 2005 and Theodora W. Greene and Peter G. M. Wuts in *"Protective Groups in Organic Synthesis"*, Wiley Interscience, 4$^{th}$ Edition 2006.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not to be viewed as limiting the scope of the invention.

The HPLC, NMR and MS data provided in the examples described below are obtained as followed: HPLC: column Waters Symmetry C8 50×4.6 mm, Conditions: MeCN/H$_2$O, 5 to 100% (8 min), max plot 230-400 nm; Mass spectra: PE-SCIEX API 150 EX (APCI and ESI), LC/MS spectra: Waters ZMD (ES); $^1$H-NMR: Bruker DPX-300 MHz.

The preparative HPLC purifications are performed with HPLC Waters Prep LC 4000 System equipped with columns Prep Nova-Pak®HR C186 μm 60 Å, 40×30 mm (up to 100 mg) or with XTerra® Prep MS C8, 10 μm, 50×300 mm (up to 1 g). All the purifications are performed with a gradient of MeCN/H$_2$O 0.09% TFA; UV detection at 254 nm and 220 nm; flow 20 mL/min (up to 50 mg). TLC Analysis is performed on Merck Precoated 60 F$_{254}$ plates. Purifications by flash chromatography are performed on SiO$_2$ support, using cyclohexane/EtOAc or DCM/MeOH mixtures as eluents.

Example 1

Formation of 2-(2-chlorophenyl)-10-(pyridin-2-ylmethyl)-2,3,8,9,10,11-hexahydro-1H-pyrazolo[4',3':3,4]pyrido[1,2-a][1,4]diazepine-1,5(7H)-dione (1) (Compound Ia, Scheme 1)

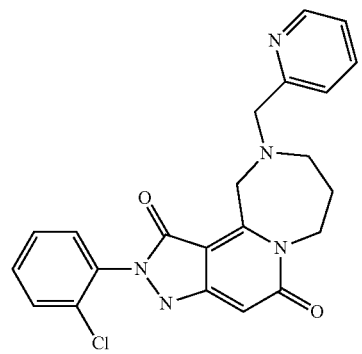 [SMILES: O=c1c2c3n(c(=O)cc2[nH]n1-c1ccccc1Cl)CCCN(Cc1ccccn1)C3]

Following the general methods as outlined in Example 3, starting from 2-chlorophenylhydrazine, dimethyl 3-oxopentanedioate, 2-chloro-1,1,1-triethoxyethane, 3-propane-1,3-diamine and pyridine-2-carbaldehyde, the title compound (1) was isolated as a yellowish solid in 32% yield (97% purity by HPLC). MS (ESI$^+$): 422.9.

Example 2

Formation of 10-benzyl-2-(2-methoxyphenyl)-2,3,8,9,10,11-hexahydro-1H-pyrazolo[4',3':3,4]pyrido[1,2-a][1,4]diazepine-1,5(7H)-dione (2)(Compound Ia, Scheme 1)

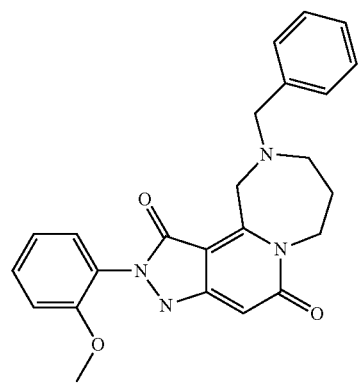 [SMILES: COc1ccccc1-n1[nH]c2cc(=O)n3c(c2c1=O)CN(Cc1ccccc1)CCC3]

Following the general methods as outlined in Example 3, starting from 2-methoxyphenylhydrazine, dimethyl 3-oxopentanedioate, 2-chloro-1,1,1-triethoxyethane, 3-propane-1,

Example 3

Formation of 10-benzyl-2-(2-chlorophenyl)-2,3,8,9,10,11-hexahydro-1H-pyrazolo[4',3':3,4]pyrido[1,2-a][1,4]diazepine-1,5(7H)-dione (3)(Compound Ia, Scheme 1)

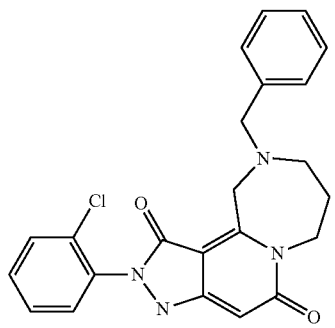 [SMILES: O=c1c2c3n(c(=O)cc2[nH]n1-c1ccccc1Cl)CCCN(Cc1ccccc1)C3]

a) methyl [1-(2-chlorophenyl)-5-hydroxy-1H-pyrazol-3-yl]acetate (Compound of Formula (VII), Scheme 1)

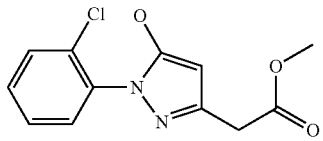

To a suspension of 2-chlorophenylhydrazine (1.82 g, 10.16 mmol, 1 eq.) in anhydrous toluene (50 ml) were added successively diisopropylethylamine (2.1 ml, 12.19 mmol, 1.2 equiv.) and dimethyl 3-oxopentanedioate (1.77 g, 10.16 mmol, 1 eq.). The resulting mixture was heated at 130-140° C. using a Dean-Stark apparatus (some wet toluene was allowed to distill off). After 2 h, the hydrazone intermediate was cleanly formed. Additional diisopropylethylamine (2.1 ml, 12.19 mmol, 1.2 eq.) was then added and the resulting mixture heated at 140° C. for 46 h using Dean-Stark system. Most of the remaining hydrazone can be removed by washings of the crude mixture with toluene. The resulting brown oil was purified by flash chromatography over SiO₂. 1.65 g of pure methyl [1-(2-chlorophenyl)-5-hydroxy-1H-pyrazol-3-yl]acetate was obtained as a yellowish solid. Yield 61%. MS (ESI⁺): 267.8; MS (ESI⁻): 265.6.

b) methyl [4-(chloroacetyl)-1-(2-chlorophenyl)-5-hydroxy-1H-pyrazol-3-yl]acetate (Compound of Formula (V), Scheme 1)

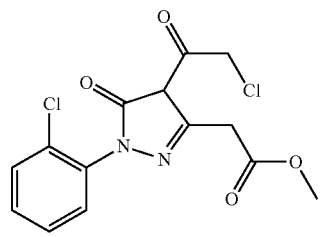 [SMILES: COC(=O)CC1=NN(c2ccccc2Cl)C(=O)C1C(=O)CCl]

The mixture of the above obtained methyl [1-(2-chlorophenyl)-5-hydroxy-1H-pyrazol-3-yl]acetate (Compound of Formula (IV), 0.60 g), was suspended in acetonitrile (5 mL) and glacial acetic acid (14 mg, 0.1 eq.) and 2-chloro-1,1,1-triethoxyethane (1.5 g) under nitrogen, was heated at 70° C. for 45-60 minutes. The resulting red solution was concentrated in vacuo to afford a red syrup that was washed with cyclohexane and then dried in vacuo. Due to its relative instability, no further purification of methyl [4-(chloroacetyl)-1-(2-chlorophenyl)-5-hydroxy-1H-pyrazol-3-yl]acetate was conducted (0.77 g, quantitative yield). MS (ESL): 344.3; MS (ESI⁻): 342.2.

c) methyl [(4Z)-4-(4-benzyl-1,4-diazepan-2-ylidene)-1-(2-chlorophenyl)-5-oxo-4,5-dihydro-1H-pyrazol-3-yl]acetate (Compound of Formula (II), Scheme 1)

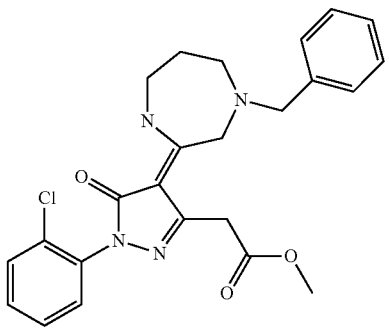 [SMILES: COC(=O)CC1=NN(c2ccccc2Cl)C(=O)/C1=C1/CN(Cc2ccccc2)CCCN1]

To a solution of the above obtained methyl [4-(chloroacetyl)-1-(2-chlorophenyl)-5-hydroxy-1H-pyrazol-3-yl]acetate (Compound of Formula (V), 1.88 mmol, 1 eq.) in 3 mL of acetonitrile was added, slowly at zero degree Celsius, N-benzylpropane-1,3-diamine (0.277 mg, 0.9 eq.). The reaction mixture was stirred at 0° C. for 0.5 h. The resulting solution was purified by silica plug using ethylacetate/0.1% triethylamine. The solvent was evaporated in vacuo and allowed to isolate a red solid which proved to be the pure methyl [(4Z)-4-(4-benzyl-1,4-diazepan-2-ylidene)-1-(2-chlorophenyl)-5-oxo-4,5-dihydro-1H-pyrazol-3-yl]acetate (0.530 g). Yield 71%. MS (ESI⁺): 454.0.

d) 10-benzyl-2-(2-chlorophenyl)-2,3,8,9,10,11-hexahydro-1H-pyrazolo[4',3':3,4]pyrido[1,2-a][1,4]diazepine-1,5(7H)-dione (Compound of Formula (Ia), Scheme 1)

An isopropanolic solution of MeONa, obtained by dissolving of sodium (0.055 g, 2.4 mmol, 2 eq.) in MeOH (3 ml) under nitrogen, was treated with methyl [(4Z)-4-(4-benzyl-1,4-diazepan-2-ylidene)-1-(2-chlorophenyl)-5-oxo-4,5-dihydro-1H-pyrazol-3-yl]acetate (Compound of Formula (II) (530 mg, 1.2 mmol, 1 eq.). The reaction mixture was stirred at room temperature for 0.5 h, then cooled, diluted with water (8 mL) and neutralized to pH 6 by addition 1M HCl solution. The precipitate was filtered off and dried under vacuo. The crude was purified by flash chromatography to yield 129 mg of pure product 10-benzyl-2-(2-chlorophenyl)-2,3,8,9,10,11-hexahydro-1H-pyrazolo[4',3':3,4]pyrido [1,2-a][1,4]diazepine-1,5(7H)-dione. Yield 26%. $^1$HNMR (500 MHz, DMSO-d6): 1.62-1.68 (m, 2H); 2.83 (t, 2H, J=7.5 Hz); 3.62-3.66 (m, 2H); 4.40-4.76 (m, 2H); 5.73 (s, 1H); 7.21-7.32 (m, 5H); 7.44-7.50 (m, 2H); 7.55-7.60 (m, 1H); 7.61-7.67 (m, 1H); 10.75-10.68 (bs, 1H). MS (ESI$^+$): 421.9.

Example 4

Formation of 10-(2-chlorobenzyl)-2-(2-chlorophenyl)-2,3,8,9,10,11-hexahydro-1H-pyrazolo[4',3':3,4]-pyrido[1,2-a][1,4]diazepine-1,5(7H)-dione (4) (Compound Ia, Scheme 1)

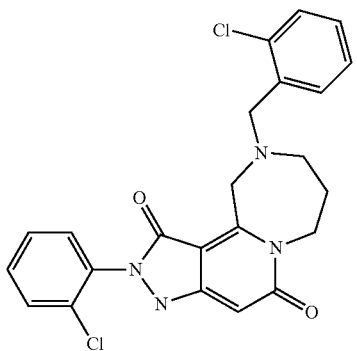 [SMILES: O=c1c2c3n(c(=O)cc2[nH]n1-c1ccccc1Cl)CCCN(Cc1ccccc1Cl)C3]

Following the general methods as outlined in Example 3, starting from 2-chlorophenylhydrazine, dimethyl 3-oxopentanedioate, 2-chloro-1,1,1-triethoxyethane, 3-propane-1,3-diamine and 2-chlorobenzaldehyde, the title compound (4) was isolated as a yellowish solid in 28% yield (98% purity by HPLC). MS (ESI$^+$): 456.3;

Example 5

Formation of 2-(2-chlorophenyl)-10-(3-methoxybenzyl)-2,3,8,9,10,11-hexahydro-1H-pyrazolo[4',3':3,4]pyrido[1,2-a][1,4]diazepine-1,5(7H)-dione (5) (Compound Ia, Scheme 1)

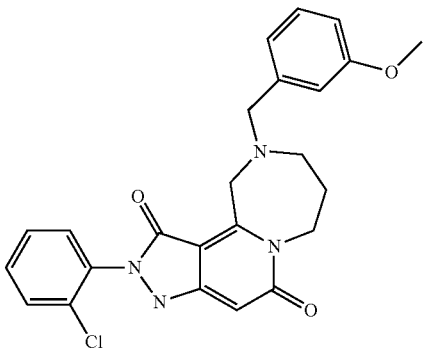 [SMILES: COc1cccc(CN2CCCn3c(c4c(=O)n(-c5ccccc5Cl)[nH]c4cc3=O)C2)c1]

Following the general methods as outlined in Example 3, starting from 2-chlorophenylhydrazine, dimethyl 3-oxopentanedioate, 2-chloro-1,1,1-triethoxyethane, 3-propane-1,3-diamine and 3-methoxybenzaldehyde, the title compound (5) was isolated as a yellowish solid in 35% yield (95% purity by HPLC). MS (ESI$^+$): 451.9.

Example 6

Formation of 10-(3-chlorobenzyl)-2-(2-chlorophenyl)-2,3,8,9,10,11-hexahydro-1H-pyrazolo[4',3':3,4]pyrido[1,2-a][1,4]diazepine-1,5(7H)-dione (6) (Compound Ia, Scheme 1)

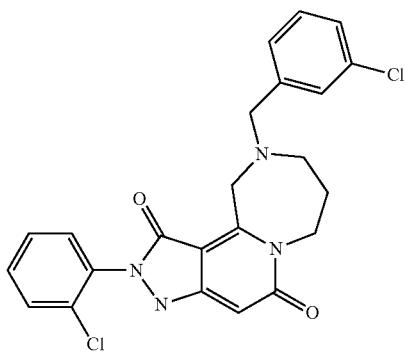 [SMILES: O=c1c2c3n(c(=O)cc2[nH]n1-c1ccccc1Cl)CCCN(Cc1cccc(Cl)c1)C3]

Following the general methods as outlined in Example 3, starting from 2-chlorophenylhydrazine, dimethyl 3-oxopentanedioate, 2-chloro-1,1,1-triethoxyethane, 3-propane-1,3- diamine and 3-chlorobenzaldehyde, the title compound (6) was isolated as a yellowish solid in 32% yield (98% purity by HPLC). MS (ESI+): 456.4;

Example 7

Formation of 2-(2-chlorophenol)-2,3,8,9,10,11-hexahydro-1H-pyrazolo[4',3':3,4]pyrido[1,2-a][1,4]diazepine-1,5(7H)-dione (7)(Compound Ia, Scheme 1)

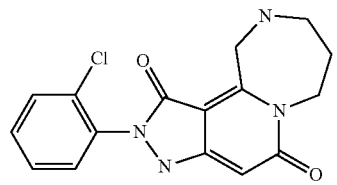 [SMILES: O=c1c2c3n(c(=O)cc2[nH]n1-c1ccccc1Cl)CCCNC3]

Following the general methods as outlined in Example 3, starting from 2-chlorophenylhydrazine, dimethyl 3-oxopentanedioate, 2-chloro-1,1,1-triethoxyethane and 3-propane-1,3-diamine, the title compound (7) was isolated as a yellowish solid in 24% yield (98% purity by HPLC). MS (ESI+): 331.9.

Example 8

Formation of tert-butyl 2-(2-chlorophenyl)-1,5-di-oxo-2,3,5,8,9,11-hexahydro-1H-pyrazolo[4',3':3,4]pyrido[1,2-a][1,4]diazepine-10(7H)-carboxylate (8) (Compound Ia, Scheme 1)

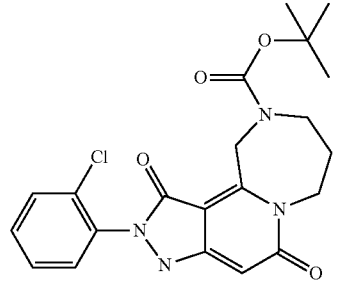 [SMILES: CC(C)(C)OC(=O)N1CCCn2c(c3c(=O)n(-c4ccccc4Cl)[nH]c3cc2=O)C1]

Following the general methods as outlined in Example 3, starting from 2-chlorophenylhydrazine, dimethyl 3-oxopentanedioate, 2-chloro-1,1,1-triethoxyethane, 3-propane-1,3-diamine and di-tert-butyl carbonate, the title compound (8) was isolated as a yellowish solid in 36% yield (97% purity by HPLC). MS (ESI+): 431.9.

Example 9

Formation of 10-(4-chlorobenzyl)-2-(2-chlorophenyl)-2,3,8,9,10,11-hexahydro-1H-pyrazolo[4',3':3,4]pyrido[1,2-a][1,4]diazepine-1,5(7H)-dione (9) (Compound Ia, Scheme 1)

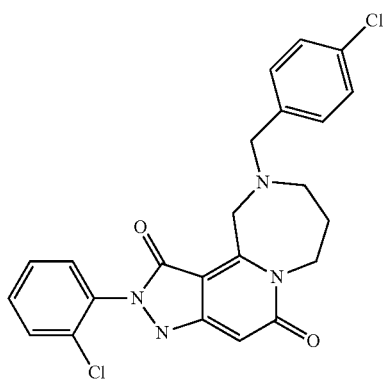 [SMILES: O=c1c2c3n(c(=O)cc2[nH]n1-c1ccccc1Cl)CCCN(Cc1ccc(Cl)cc1)C3]

Following the general methods as outlined in Example 3, starting from 2-chlorophenylhydrazine, dimethyl 3-oxopentanedioate, 2-chloro-1,1,1-triethoxyethane, 3-propane-1,3-diamine and 4-chlorobenzaldehyde, the title compound (9) was isolated as a yellowish solid in 30% yield (98% purity by HPLC). MS (ESI+): 456.4.

Example 10

Formation of 2-(2-chlorophenyl)-10-(2-methoxybenzyl)-2,3,8,9,10,11-hexahydro-1H-pyrazolo[4',3':3,4]pyrido[1,2-a][1,4]diazepine-1,5(7H)-dione (10) (Compound Ia, Scheme 1)

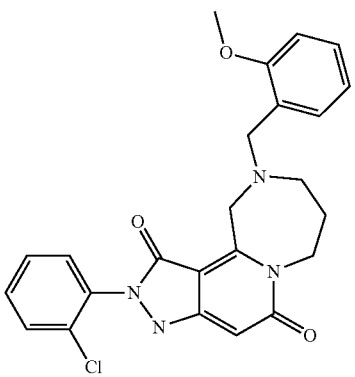 [SMILES: COc1ccccc1CN1CCCn2c(c3c(=O)n(-c4ccccc4Cl)[nH]c3cc2=O)C1]

Following the general methods as outlined in Example 3, starting from 2-chlorophenylhydrazine, dimethyl 3-oxopentanedioate, 2-chloro-1,1,1-triethoxyethane, 3-propane-1,3-diamine and 2-methoxybenzaldehyde, the title compound

(10) was isolated as a yellowish solid in 33% yield (94% purity by HPLC). MS (ESI⁺): 451.9.

Example 11

Formation of 2-(2-chlorophenyl)-10-(4-methoxybenzyl)-2,3,8,9,10,11-hexahydro-1H-pyrazolo[4',3':3,4]pyrido[1,2-a][1,4]diazepine-1,5(7H)-dione (11) (Compound Ia, Scheme 1)

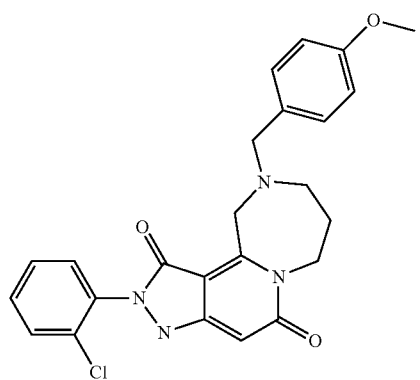 [SMILES: COc1ccc(CN2CCCn3c(c4c(=O)n(-c5ccccc5Cl)[nH]c4cc3=O)C2)cc1]

Following the general methods as outlined in Example 3, starting from 2-chlorophenylhydrazine, dimethyl 3-oxopentanedioate, 2-chloro-1,1,1-triethoxyethane, 3-propane-1,3-diamine and 4-methoxybenzaldehyde, the title compound (11) was isolated as a yellowish solid in 32% yield (96% purity by HPLC). MS (ESI⁺): 451.9.

Example 12

Formation of 2-(2-chlorophenyl)-10-(furan-3-ylmethyl)-2,3,8,9,10,11-hexahydro-1H-pyrazolo[4',3':3,4]pyrido[1,2-a][1,4]diazepine-1,5(7H)-dione (12) (Compound Ia, Scheme 1)

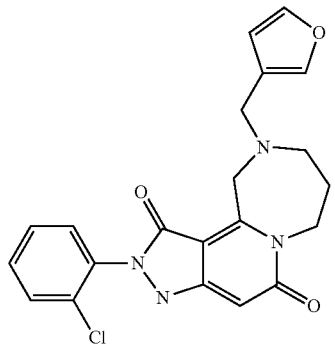 [SMILES: O=c1c2c3n(c(=O)cc2[nH]n1-c1ccccc1Cl)CCCN(Cc1ccoc1)C3]

Following the general methods as outlined in Example 3, starting from 2-chlorophenylhydrazine, dimethyl 3-oxopentanedioate, 2-chloro-1,1,1-triethoxyethane, 3-propane-1,3-diamine and furan-3-carbaldehyde, the title compound (12) was isolated as a yellowish solid in 32% yield (95% purity by HPLC). MS (ESI⁺): 411.9.

Example 13

Formation of 9-benzyl-2-(2-chlorophenol)-2,3,7,8,9,10-hexahydro pyrazolo[4',3':3,4]pyrido[1,2-a]pyrazine-1,5-dione (13)(Compound Ia, Scheme 1)

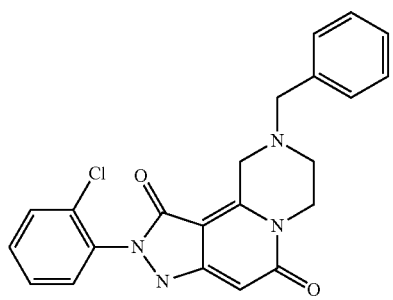 [SMILES: O=c1c2c3n(c(=O)cc2[nH]n1-c1ccccc1Cl)CCN(Cc1ccccc1)C3]

Following the general methods as outlined in Example 3, starting from 2-chlorophenylhydrazine, dimethyl 3-oxopentanedioate, 2-chloro-1,1,1-triethoxyethane and N-benzylethane-1,2-diamine, the title compound (13) was isolated as a yellowish solid in 18% yield (90% purity by HPLC). MS (ESI⁺): 408.0.

Example 14

Formation of 2-(2-chlorophenol)-2,3,7,8-tetrahydro-1H-pyrazolo[4',3':3,4]pyrido[2,1-c][1,4]oxazine-1,5 (10H)-dione (14)(Compound Ia, Scheme 1)

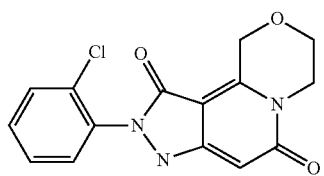 [SMILES: O=c1c2c3n(c(=O)cc2[nH]n1-c1ccccc1Cl)CCOC3]

Following the general methods as outlined in Example 3, starting from 2-chlorophenylhydrazine, dimethyl 3-oxopentanedioate, 2-chloro-1,1,1-triethoxyethane and 2-aminoetha-

Example 15

Formation of 2-(2-methoxyphenyl)-10-(pyridin-2-ylmethyl)-2,3,8,9,10,11-hexahydro-1H-pyrazolo[4',3':3,4]pyrido[1,2-a][1,4]diazepine-1,5(7H)-dione (15) (Compound Ia, Scheme 1)

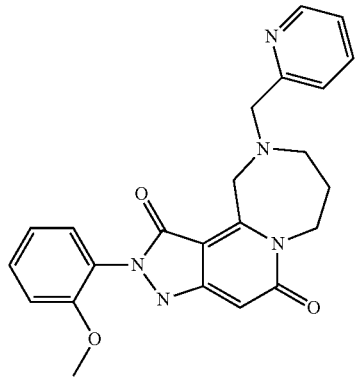 [SMILES: COc1ccccc1-n1[nH]c2cc(=O)n3c(c2c1=O)CN(Cc1ccccn1)CCC3]

Following the general methods as outlined in Example 3, starting from 2-methoxyphenylhydrazine, dimethyl 3-oxopentanedioate, 2-chloro-1,1,1-triethoxyethane, 3-propane-1,3-diamine and pyridine-2-carbaldehyde, the title compound (15) was isolated as a yellowish solid in 30% yield (94% purity by HPLC). MS (ESI+): 418.6.

Example 16

Formation of 10-(3-methoxybenzyl)-2-(2-methoxyphenyl)-2,3,8,9,10,11-hexahydro-1H-pyrazolo[4',3':3,4]pyrido[1,2-a][1,4]diazepine-1,5(7H)-dione (16) (Compound Ia, Scheme 1)

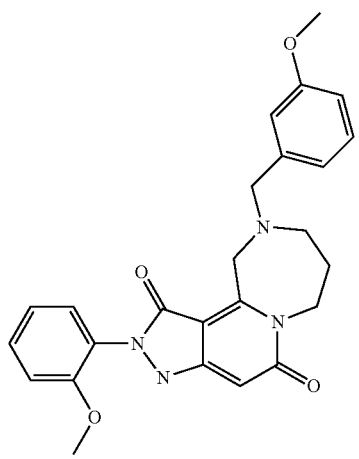 [SMILES: COc1cccc(CN2CCCn3c(c4c(=O)n(-c5ccccc5OC)[nH]c4cc3=O)C2)c1]

Following the general methods as outlined in Example 3, starting from 2-methoxyphenylhydrazine, dimethyl 3-oxopentanedioate, 2-chloro-1,1,1-triethoxyethane, 3-propane-1,3-diamine and 3-methoxybenzaldehyde, the title compound (16) was isolated as a yellowish solid in 33% yield (97% purity by HPLC). MS (ESI+): 447.6.

Example 17

Formation of 2-(2-chlorophenyl)-10-[(1-methyl-1H-pyrazol-3-yl)methyl]-2,3,8,9,10,11-hexahydro-1H-pyrazolo[4',3':3,4]pyrido[1,2-a][1,4]diazepine-1,5(7H)-dione (17)(Compound Ia, Scheme 1)

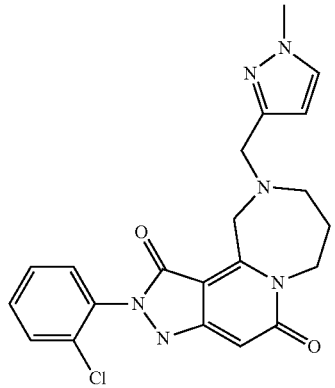 [SMILES: Cn1ccc(CN2CCCn3c(c4c(=O)n(-c5ccccc5Cl)[nH]c4cc3=O)C2)n1]

Following the general methods as outlined in Example 3, starting from 2-chlorophenylhydrazine, dimethyl 3-oxopentanedioate, 2-chloro-1,1,1-triethoxyethane, 3-propane-1,3-diamine and 1-methyl-1H-pyrazole-3-carbaldehyde, the title compound (17) was isolated as a yellowish solid in 29% yield (93% purity by HPLC). MS (ESI+): 425.9.

Example 18

Formation of 2-(2-chlorophenyl)-10-(pyridin-3-ylmethyl)-2,3,8,9,10,11-hexahydro-1H-pyrazolo[4',3':3,4]pyrido[1,2-a][1,4]diazepine-1,5(7H)-dione (18) (Compound Ia, Scheme 1)

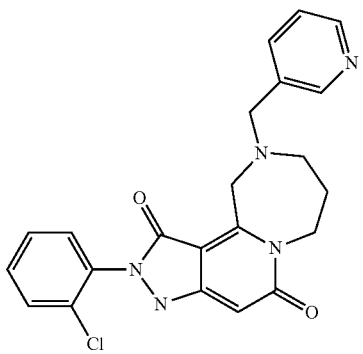 [SMILES: O=c1c2c3n(c(=O)cc2[nH]n1-c1ccccc1Cl)CCCN(Cc1cccnc1)C3]

Following the general methods as outlined in Example 3, starting from 2-chlorophenylhydrazine, dimethyl 3-oxopentanedioate, 2-chloro-1,1,1-triethoxyethane, 3-propane-1,3-diamine and pyridine-3-carbaldehyde, the title compound (18) was isolated as a yellowish solid in 30% yield (98% purity by HPLC). MS (ESI+): 422.9.

Example 19

Measurement of Levels of Reactive Oxygen Species in Different Cell Cultures

The activity of the compounds according to the invention may be tested for their activity in the inhibition or reduction of formation of reactive oxygen species (ROS) from oxygen in cells. The activity of the compounds is tested in the following cell cultures by different techniques such as nitroblue tetrazolium, Amplex Red, Chemiluminescence (Luminol) and 2',7'-dichlorodihydrofluorescein diacetate ($H_2$DCF-DA) according to the protocols detailed below.

Human Microglia Cell Line

Human microglia cell line (HMC3, human microglia clone 3) (Janabi et al., 1995, *Neurosci. Lett.* 195:105) were cultured in MEM (Eagle's minimum essential medium) containing 10% FBS with 50 U/ml penicillin G sodium 50 µg/ml streptomycin sulfate, and incubated at 37° C. for 24 hours. IFN-γ (human IFN-γ, Roche. 11 040 596 001) was added to the culture medium for a final concentration of 10 ng/ml 24 h, before detection of $O_2$ formation.

Human Umbilical Vein Endothelial Cells (HUVEC)

HUVEC are cultured in endothelial basal medium supplemented with hydrocortisone (1 µg/mL, CalbioChem), bovine brain extract (12 µg/mL), gentamicin (50 µg/mL, Calbio-Chem), amphotericin B (50 ng/mL, CalBioChem EGF (10 ng/mL, and 10% FCS until the fourth passage. When the fifth passage was started, cells were cultured with a lower concentration of FCS (2%) in the absence of EGF, if not indicated otherwise. All experiments were done with cells of the fifth passage. The cells were incubated with OxLDL (oxidized low-density lipoprotein) or its buffer as control for 24 h, before detection of $O_2^-$ formation.

HL-60 Cells

Human acute myeloid leukemia cell line HL-60 was cultured in RPMI 1640 (Invitrogen) supplemented with 10% heat-inactivated calf serum, 2 mM glutamine, 100 U/mL penicillin (Sigma), and 100 µg streptomycin (Sigma) at 37° C. under a humidified atmosphere of 5% $CO_2$. HL60 differentiation to the neutrophil phenotype was triggered by adding $Me_2$SO (final concentration 1.25% v/v for 6 days) to the culture medium.

1. Nitroblue Tetrazolium (NBT)

Intracellular and extracellular superoxide was measured by a colorimetric technique using a quantitative nitroblue tetrazolium (NBT) test. SOD-inhibitable conversion of NBT to formazan, a fine blue precipitate, in the presence of superoxide anion was measured using Fluostar Optima spectrometer (BMG labtech). Following incubation with appropriate stimuli, cells were trypsinized (1× Trypsin-EDTA), collected by centrifugation, and washed with PBS to remove medium. 5×10$^5$ cells were plated on 48-well plates and incubated in Hank's balanced salt solution containing 0.5 mg/mL NBT with or without 800 U/mL SOD in the presence or absence of compounds according to the invention. As a control, DPI was included at a final concentration of 10 µM. After 2.5 h, cells were fixed and washed with methanol to remove non reduced NBT. The reduced formazan was then dissolved in 230 µl of 2M potassium hydroxide and in 280 µl of dimethylsulfoxide. The absorption was measured at 630 nm. For calculation, the absorbance at 630 nm was normalized for each individual well. The mean of the four blank values was subtracted from each corrected value for each time point. NOX activities were expressed as % of the activity in control cells. Residual activity of DPI-treated cells was usually <10%.

2. Amplex Red

Extracellular hydrogen peroxide was measured using Amplex UltraRed (Molecular Probes). Cells were trypsinized (1× Trypsin-EDTA), collected by centrifugation, and resuspended in HBSS supplemented with 1% glucose. Cells were seeded into black 96-well plates at a density of 50,000 cells in 200 µl testing buffer (HBSS 1% glucose containing 0.005 U/mL horseradish peroxidase (Roche) and 50 µM Amplex Red in the presence or absence of compounds according to the invention. As a control, DPI was included at a final concentration of 10 µM The plates were placed in the fluorescent Optima Fluorescent plate reader and kept at 37° C. during 20 min. Fluorescence was measured for 15 min hours with excitation and emission wavelengths of 544 nm and 590 nm respectively. NOX activities were expressed as % of the activity in control cells. Residual activity of DPI-treated cells was usually <10%.

The Table 1 below summarizes the percentage of inhibition of NOX activity as measured by Amplex Red using DMSO-differentiated HL60 cells as described above:

TABLE 1

| Compound n° | Inhibition (%) |
| --- | --- |
| (1) | 86 |
| (2) | 81 |
| (5) | 80 |
| (7) | 86 |
| (8) | 85 |
| (12) | 77 |
| (13) | 81 |
| (14) | 83 |
| (15) | 87 |

The Table 2 below summarizes the IC$_{50}$ of NOX activity as measured by Amplex Red using DMSO-differentiated HL60 cells as described above:

TABLE 2

| Compound n° | IC$_{50}$ (µM) |
| --- | --- |
| (1) | <5 |
| (2) | <5 |
| (5) | <5 |
| (7) | <5 |
| (8) | <5 |
| (12) | <5 |

3. Chemiluminescence (Luminol)

ROS was measured using the chemiluminescent probe luminol. Cells were cultured and plated as for Amplex Red except that the Amplex Red agent was replaced by 10 µg/mL luminol (Sigma 09235). Light emission was recorded continuously at 37° C. for 60 minutes using the luminescence function of the FluoStar Optima fluorescent plate reader. The mean of the four blank values was subtracted from each corrected value for each time point. NOX activities were expressed as % of the activity in control cells. Residual activity of DPI-treated cells was usually <10%.

4. 2',7'-dichlorodihydrofluorescein diacetate ($H_2$DCF-DA)

HUVEC were plated on coverslips and made quiescent overnight in 0.5% BSA before stimulation with TGF-β. Cells were loaded for 10 minutes with 5 µM CM-H2DCFDA in phenol-red-free medium in the dark and then treated with TGF-β (R&D Systems) in the presence or absence of compounds according to the invention. Cells were then visualized by immunofluorescence microscopy after fixation and staining of the nuclei with DAPI or examined live using confocal microscopy. DCF fluorescence was visualized at an excitation wavelength of 488 nm and emission at 515 to 540 nm. To avoid photo-oxidation of the indicator dye, images were collected with a single rapid scan using identical parameters for all samples. For calculation, the absorbance at 540 nm was normalized to absorbance at 540 nm for each individual well. The mean of the four blank values was subtracted from each corrected value for each time point. NOX activities were expressed as % of the activity in control cells. Residual activity of DPI-treated cells was usually <10%.

Example 20

Blood Pressure Measurement in Spontaneous Hypertensive Rats (SHR)

In order to test the ability of compounds according to the invention to treat hypertension, the following assay is carried out.

SHR at 11 weeks of age with systolic blood pressure above 170 mmHg are used. Compound according to the invention are administered orally to rats at a dose of about 3, 10, 30 and 100 mg/kg between 10:00 and 12:00 h. Mean, systolic and diastolic blood pressure and heart rate are monitored 2, 4, 6, 8 and 24 hours after the first administration of a compound according to the invention in order to perform a kinetic analysis over one day.

After that, blood pressure is monitored every two days for two weeks, in the morning at 24 h time point and at the half life of the compound.

After the last injection, a 24 hour time point is monitored. The animals are controlled for an additional week without treatment in order to monitor the compound withdrawal. The animals are treated once a day for a period of two weeks by gavage with a special needle adapted for gavage at 5 ml/kg. Before using the animals, they are acclimated for two days and further trained during one week. The blood pressure is measured in awaken rats by tail-cuff plethysmography (Codas 6, Kent). Animals are included into groups after training for several days and if SBP variability was ≤40 mm Hg, i.e. +/−20 mm Hg. Baseline measurements were performed at least on two days before the experiment. Before the beginning of the experiment, animals are randomized in order to constitute homogeneous groups.

Example 21

Bleomycin-Induced Lung Injury in Mice

In order to test the ability of compounds according to the invention to prevent or treat respiratory disorder or disease, the following assay is carried out.

In order to produce pulmonary lesion which are comparable to those in respiratory disorder or disease such as idiopathic pulmonary fibrosis, animals receive endotracheally a single sublethal dose of bleomycin (BLM) (0.0125 UI per mouse dissolved in 40 µl of 0.9% NaCl). Control animals are subjected to the same protocol but received the same volume of intratracheal saline instead of BLM. Tracheal instillation is carried out under ketamin (80 mg/kg of body weight, i.p.) and xylazine (20 mg/kg de body weight, i.p.) anesthesia.

5 weeks days after endotracheal BLM or saline, the animals are killed by a lethal injection of sodium pentobarbital followed by exsanguination of abdominal aorta. Lungs are weighed and processed separately for biochemical (n=10 lungs per group) and histological studies (n=5 per group) as indicated below. The animals are randomly divided into four groups: control-saline (n=8) and control+BLM (n=15); Compound Dose 1+BLM (n=15) and Compound Dose 2+BLM (N=15). Treatments vehicle or compounds are administered for 5 weeks.

Mice are treated by daily oral administration of compound according to the invention or saline/control starting on day 0 for five weeks in the preventive model and starting on day 10 up to five weeks for the curative model. Whole lung accumulation of acid-soluble collagen is analyzed by Sircol assay.

Preventive Model

The broad lines of the above protocol were followed. At day 0, animals received an intratracheal injection of 0.0125 UI of bleomycin (20 µl) to produce pulmonary lesions. Preventive treatment group was orally administered a compound of the invention once a day for five weeks starting also at day 0. The animals are randomly divided into four groups: control-saline (n=11); control+BLM (n=12); Compound 3 of the invention per os 40 mg/kg+BLM (n=12) and Pirfenidone (AQCHEM, ref P1002) (antifibrotic agent known for its activity in multiple fibrotic conditions, including those of the lung, kidney and liver) at 100 mg/kg per os+BLM (n=12). 35 days after endotracheal BLM or saline, the animals are killed and lungs are processed as indicated above for quantification of collagen deposition and lung inflammation by SIRCOL assay (TebuBio, ref S1000). Compound 3 at a dose of 40 mg/kg was able to inhibit collagen deposition of 46% as compared to bleomycin control to a comparable extend to Pirfenidone at 100 mg/kg (45%).

Curative Model

The broad lines of the above protocol were followed. At day 0, animals received an intratracheal injection of 0.0125 UI of bleomycin (40 µl) to produce pulmonary lesions. Curative treatment group was orally administered a compound of the invention once a day for 3.5 weeks starting from day 10 to day 35. The animals are randomly divided into six groups: control-saline (n=8); 2 groups control+BLM (n=13); Compound 3 of the invention per os 40 mg/kg+BLM (n=13); Compound 3 of the invention per os 10 mg/kg+BLM (n=13) and Pirfenidone (AQCHEM, ref P1002) at 100 mg/kg per os+BLM (n=13). One bleomycin control group was stopped at day 10, the animals were killed and collagen levels were measured. For the other groups, 35 days after endotracheal BLM or saline, the animals are killed and lungs are processed as indicated above for quantification of collagen deposition and lung inflammation as indicated above. Compound 3 at doses of 40 mg/kg and 10 mg/kg was able to inhibit collagen deposition of 52% and 64%, respectively, as compared to bleomycin control to a much higher extend than Pirfenidone at 100 mg/kg (12%).

Therefore, those results strongly support the preventive and curative effect of compounds of the invention in respiratory disorder or disease such as lung fibrosis.

Example 22

Animal Models of Cancer

In order to test the ability of compounds according to the invention to treat cancers, in particular to reduce tumour growth and/or angiogenesis, the following assays are carried out.

In Vivo Angiogenesis Assay 7 to 10 weeks old C57BL6/J females are injected subcutaneously with 400 µl of Matrigel growth factor reduced complemented with 500 ng/ml of angiogenic factor (b-FGF or VEGF). One week after the graft, mice are scanned using MicroCT (Skyscan). Mice are injected retro-orbitally with a tracer (400 μl iodated liposomes) to visualize the vessel density. Scan picture are then reconstituted with Recon program and the density of grey in the plug is counted in all the slide of the plug. Compounds of the invention are administered per oral route at the appropriate doses 1 and 2, once-a-day for 10 days. Results are expressed in grey density, which is correlated to vessel density. Matrigel plug are also frozen and stained for CD31 to visualize vessels.

Tumour Growth Assay $5.10^5$ Lewis Lung Carcinoma cells (LLC1) are injected subcutaneously in the back of mice. Mice are treated with a compound according to the invention at 40 mg/kg everyday per os. When the control tumour reaches about 1 cm length, mice are sacrificed and tumour are recovered, weight and frozen. For therapeutic assay, mice are injected with LLC1 cells since tumours have grown about 0.5 cm mice are treated and tumour size is assessed every day. After sacrifice, tumour and frozen and sections of tumour are stained with anti-CD31 antibody and ROS level is analyzed.

Example 23

Effect on Human Lung Fibroblasts (IMR-90)

In order to test the ability of compounds according to the invention to prevent or treat respiratory disorder or disease, the following assay is carried out.

α-SMA Protein Expression

The activity of compounds of the invention is investigated through their effect on the TGFβ-induced differentiation of human lung fibroblasts to myofibroblasts by quantification of α-SMA protein expression in IMR-90 cells.

IMR-90 cells (ATCC (LGC), ref ATCC-CCL-186) were cultured in Eagle's Minimum Essential Medium (EMEM) supplemented with 10% Fetal Calf Serum (FCS) at 37° C. in air with 5% $CO_2$. Cells reaching 75-80% confluence were passaged using a mixture of trypsin-EDTA. Cells were seeded in 6-well plates at a density of 200,000 cells per well and cultured for 24 h in EMEM supplemented with 10% FCS. Cells were then starved by replacing medium with EMEM without FCS. After 24 h, cells were treated with a compound according to the invention (0.1, 1 and 10 μM). After 1 h, cells were exposed to TGFβ (2.5 ng/ml) for 48 h. The compound and TGFβ stock solutions were prepared in EMEM. The DMSO concentration in the culture media was 1% final. Controls were treated with vehicle (DMSO). On the day of harvest, cells were washed with ice-cold PBS and detached with a cell scraper in 1.1 ml of PBS supplemented with protease inhibitors (Complete, Roche). Cells were centrifuged at 10,000×g for 10 mM at 4° C. Cell pellets were homogenized in 65 μl of RIPA lysis buffer (Sigma) (150 mM NaCl, 1.0% IGEPAL® CA-630, 0.5% sodium deoxycholate, 0.1% SDS, 50 mM Tris, pH 8.0) supplemented with protease inhibitors (Complete, Mini Protease Inhibitor Cocktail Tablets, Roche ref 11836153001, list of protease inhibitor available on request to the supplier) and briefly sonicated. Lysates were frozen and kept at −80° C. until analysis. Proteins in solution were measured by Bradford assay (Sigma, ref B6919) and diluted at a final concentration of 0.25 μg/μl in a mixture of RIPA buffer and loading buffer (Tris-base 0.31 M, glycerol 10%, SDS 2%, β-mercaptoethanol 5%, bromophenol blue 0.002%). Samples were heated at 95° C. for 5 min and proteins were separated using NuPage 12% Bis-Tris gels and MOPS running buffer (50 mM MOPS, 50 mM Tris, 3.5 mM sodium dodecyl sulphate, 0.8 mM EDTA) at a constant voltage (200 V, 60 min). Proteins were transferred for 75 min at constant voltage (35 V) onto rehydrated nitrocellulose membranes under wet conditions using Transfer buffer (Invitrogen). Membranes were blocked with 5% non-fat dry milk in PBS-Tween (0.05% Tween). After blocking, the membranes were incubated overnight with primary antibodies (Anti-α-SMA) diluted in 3% dry milk and PBS-T. Anti-α-SMA antibody (RnDsystem, MAB1420) was diluted 1:3000. The membranes were then rinsed with PBS and incubated 1 h with GAPDH primary antibody (SantaCruz, sc47724) diluted 1/3,000 in 3% dry milk and PBS-T, to demonstrate equal loading of proteins in each lane. The membranes were then washed with PBS-T and probed with horseradish peroxidase conjugated goat anti-mouse IgG (1:4,000). A third wash was performed and blots were developed by chemiluminescence (ECL; Amersham Biosciences, Buckinghamshire, UK). The autoradiograms were scanned with an image scanner and processed by image analysis using the public domain NIH ImageJ program (http://rsbweb.nih.gov/ij/; Vittal, 2007, JPET; 321:35-44). Data were acquired in arbitrary densitometric units and transformed to percentages of the densitometric levels obtained from scans of control samples visualized on the same blots. The intensity of α-SMA was correlated against the intensity of GAPDH. Data were expressed as mean±SEM and statistical comparison between 2 groups was done with Student's t-test.

HSP-47 Protein Expression

The activity of compounds of the invention is investigated through their effect on the TGFβ-induced differentiation of human lung fibroblasts to myofibroblasts by quantification of HSP-47 protein expression in IMR-90 cells.

IMR-90 cells were cultured, seeded, starved and treated with a compound according to the invention as indicated above.

On the day of harvest, cells were processed as indicated above. After blocking, the membranes were incubated overnight as described above. Anti-Hsp47 antibody (Abcam, ab13510) was diluted 1:3000. The membranes were then rinsed as described above. The autoradiograms were analysed as described above. The intensity of Hsp47 was correlated against the intensity of GAPDH.

Compound 3 was able to inhibit biomarkers of human myofibroblast differentiation (α-SMA) and extracellular matrix accumulation (HSP47) in a concentration range of 0.1-20 μM (21 to 51% and 89 to 77%, respectively). Therefore, those results strongly support the effect of compound 3 of the invention in disorder or disease involving fibrosis mechanism such as lung fibrosis.

Col3a mRNA Levels

The activity of compounds of the invention is investigated through their effect on the TGFβ-induced differentiation of human lung fibroblasts to myofibroblasts by quantification of Col3a mRNA levels in IMR-90 cells.

IMR-90 cells were cultured as indicated above. The medium was changed every three days. Cells reaching 75-80% confluence were passaged using a mixture of trypsin-EDTA. Only IMR-90 cells from passage number eight or less were used to prevent spontaneous differentiation.

For RNA isolation, IMR-90 cells were plated on 6-well plates at 200,000 cells/well and were grown in complete EMEM medium for 24 h. The following day cells were growth-arrested by removing the FBS from the medium. Cells were exposed to a compound according to the invention at a final concentration of 0.1 and 20 μM one hour prior to treatment with TGFβ3. To achieve differentiation to myofibroblast, IMR-90 cells were incubated for 24 h with TGFβ3 at a concentration of 2.5 ng/ml. The compound and TGFβ stock solutions were prepared as above. The DMSO concentration and controls were as above.

Total RNA was isolated using RNeasy Mini (Qiagen, ref 74104) kit according to the manufacturer's instructions. Briefly, cell lysate was homogenised using a 20-gauge needle in presence of RLT lysis buffer provided by the RNeasy Mini Kit and transferred to a QIAshredder (Qiagen, ref 79654) column to complete the homogenization. Ethanol is then added to the lysate, creating conditions that promote selective binding of RNA to the RNeasy membrane. The sample is then applied to the RNeasy spin column Total RNA binds to the membrane. Residual genomic DNA was removed by incubating the RNA sample with 30 units of DNase (Qiagen, ref 79254) for 15 min at room temperature. Contaminants are efficiently washed away by wash steps with washing buffer provided by the RNeasy Mini Kit. RNA samples were diluted to 100 ng/μl in DEPC water. Reverse transcription to cDNA was undertaken using 5000 ng of total RNA using PrimerScript (Takara, ref DRR027sp) reverse transcriptase according to the manufacturer's protocol. Expression of COL3a was analysed by quantitative real-time PCR. Amplifications were performed in a 10 μl final reaction volume containing 2×SYBR Green I Master Mix (Applied Biosystems, ref 4309155) buffer, 0.3 mM of each specific primer, the cDNA template (500 ng total RNA) and H$_2$O (sterile PCR grade).

Primers were designed using the Primer Express® 2.0 Software (Applied Biosystems) and were synthesised by Invitrogen. PCR primers for human COL3a were:

```
Col3a forward primer:
5' TTA AAG GAA AGA CAC TCC GAT CAG AGA TGA

3'-Col3a reverse primer:
5' AAT GTT TCC GGA GTA GGG GAG TCT TTT T 3'
```

PCR reactions were run on an ABI Prism® 7900 Ht detection system (Applied Biosystems). The amplification program included the initial denaturation step at 95° C. for 10 min and 45 cycles of denaturation at 95° C. for 15 s, annealing at 60° C. for 1 min, and extension at 72° C. for 1 min. The temperature transition rate was 20° C./s. Fluorescence was measured at the end of each cycle. After amplification, melting curves were acquired to determine the specificity of the PCR. This analysis was performed in triplicate on RNA samples from each condition.

Transcript levels obtained for COL3a were normalised to transcript levels for alpha subunit of the elongation factor-1 complex (EEF1A), beta glucoronidase (GUSB) and beta microtubulin using the geNorm software (Vandesompele et al., 2002, *Genome Biol.*, June 18; 3(7)).

Data were transformed to fold increase compared to the transcript levels obtained from control samples. Data were expressed as mean±SEM and statistical comparison between 2 groups was done with Student's t-test.

PLOD2 mRNA Levels

The activity of compounds of the invention is investigated through their effect on the TGFβ-induced differentiation of human lung fibroblasts to myofibroblasts by quantification of PLOD2 mRNA levels in IMR-90 cells.

IMR-90 cells were cultured as indicated above. The medium was changed every three days. Cells reaching 75-80% confluence were passaged using a mixture of trypsin-EDTA. Only IMR-90 cells of passage number eight or less were used to prevent spontaneous differentiation.

For RNA isolation and reverse transcription to cDNA, the same protocols as above were followed. The expression of PLOD2 was analysed as for COL3a.

PCR primers for human PLOD2 were:

```
PLOD2 forward primer:
5' TGG CTA CTT CTC GCT CTG CT 3'

PLOD2 reverse primer:
5' TTC CTG TTG TGC CAA AAT AAT AGT G 3'
```

Data were analyzed as set above.

Compound 3 was able to inhibit biomarkers of collagen accumulation (Col13a) and collagen fiber cross-linking enzyme (PLOD2) in a concentration range of 0.1-20 μM (0 to 57% and 1% to 36%, respectively). Compound 3 inhibited the TGFβ-induced increase of Col3a and PLOD2 mRNA levels in lung fibroblast (IMR-90) cells. These data indicate that Compound 3 can inhibit TGFβ-induced differentiation of fibroblasts to myofibroblasts and subsequent overproduction of collagen.

Therefore, those results strongly support therapeutic effect of compounds of the invention in respiratory disorder or disease such as lung fibrosis.

The invention claimed is:
1. A pyrazoline di one compound according to Formula (I):

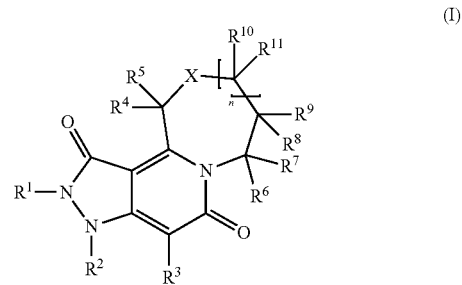

$R^1$ is selected from H; optionally substituted alkoxycarbonyl; optionally substituted $C_1$-$C_6$ alkyl; optionally substituted $C_2$-$C_6$ alkenyl; optionally substituted $C_2$-$C_6$ alkynyl; optionally substituted alkoxy; optionally substituted alkoxy $C_1$-$C_6$ alkyl; optionally substituted aminoalkyl; optionally substituted acyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; $R^2$ is selected from H; optionally substituted alkoxycarbonyl; optionally substituted acyl; optionally substituted acyl $C_1$-$C_6$ alkyl; optionally substituted $C_1$-$C_6$ alkyl; optionally substituted $C_2$-$C_6$ alkenyl; optionally substituted $C_2$-$C_6$ alkynyl; optionally substituted aryl; optionally substituted heteroaryl; optionally substituted $C_3$-$C_8$-cycloalkyl; optionally substituted heterocycloalkyl; optionally substituted $C_3$-$C_8$-cycloalkyl $C_1$-$C_6$ alkyl; optionally substituted heterocycloalkyl $C_1$-$C_6$ alkyl; optionally substituted aryl $C_1$-$C_6$ alkyl and optionally substituted heteroaryl $C_1$-$C_6$ alkyl; $R^3$ is selected is selected from H; optionally substituted alkoxycarbonyl; optionally substituted acyl; optionally substituted $C_1$-$C_6$ alkyl; optionally substituted $C_2$-$C_6$ alkenyl;

optionally substituted C$_2$-C$_6$ alkynyl; optionally substituted aryl; optionally substituted C$_1$-C$_6$ alkyl aryl; optionally substituted aryl C$_1$-C$_6$ alkyl; optionally substituted heteroaryl; optionally substituted C$_1$-C$_6$ alkyl heteroaryl; optionally substituted heteroaryl C$_1$-C$_6$ alkyl; optionally substituted C$_2$-C$_6$ alkenyl aryl; optionally substituted aryl C$_2$-C$_6$ alkenyl; optionally substituted C$_2$-C$_6$ alkenyl heteroaryl; optionally substituted heteroaryl C$_2$-C$_6$ alkenyl; optionally substituted C$_3$-C$_8$-cycloalkyl; optionally substituted heterocycloalkyl; optionally substituted C$_1$-C$_6$ alkyl C$_3$-C$_8$-cycloalkyl; optionally substituted C$_3$-C$_8$-cycloalkyl C$_1$-C$_6$ alkyl; optionally substituted C$_1$-C$_6$ alkyl heterocycloalkyl and optionally substituted heterocycloalkyl C$_1$-C$_6$ alkyl; R$^4$, R$^5$, R$^6$, R$^7$, R$^8$ and R$^9$ are independently selected from H; halogen; nitro; optionally substituted C$_1$-C$_6$ alkyl; optionally substituted C$_2$-C$_6$ alkenyl; optionally substituted C$_2$-C$_6$ alkynyl; optionally substituted amino; optionally substituted aminoalkyl; optionally substituted alkoxy; and optionally substituted alkoxy C$_1$-C$_6$ alkyl; R$^{10}$ is selected from H and optionally substituted C$_1$-C$_6$ alkyl; R$^{11}$ is selected from H; optionally substituted alkoxycarbonyl; optionally substituted acyl; optionally substituted C$_1$-C$_6$ alkyl; optionally substituted C$_2$-C$_6$ alkenyl; optionally substituted C$_2$-C$_6$ alkynyl; optionally substituted alkoxy; optionally substituted alkoxy C$_1$-C$_6$ alkyl; optionally substituted aminoalkyl; optionally substituted acyl; optionally substituted aryl; optionally substituted C$_1$-C$_6$ alkyl aryl; optionally substituted aryl C$_1$-C$_6$ alkyl; optionally substituted heteroaryl; optionally substituted C$_1$-C$_6$ alkyl heteroaryl; optionally substituted heteroaryl C$_1$-C$_6$ alkyl; optionally substituted C$_2$-C$_6$ alkenyl aryl; optionally substituted aryl C$_2$-C$_6$ alkenyl; optionally substituted C$_2$-C$_6$ alkenyl heteroaryl; optionally substituted heteroaryl C$_2$-C$_6$ alkenyl; optionally substituted C$_3$-C$_8$-cycloalkyl; optionally substituted heterocycloalkyl; optionally substituted C$_1$-C$_6$ alkyl C$_3$-C$_8$-cycloalkyl; optionally substituted C$_3$-C$_8$-cycloalkyl C$_1$-C$_6$ alkyl; optionally substituted C$_1$-C$_6$ alkyl heterocycloalkyl and optionally substituted heterocycloalkyl C$_1$-C$_6$ alkyl; R$^{12}$ is selected from H; —Z—NR$^{13}$R$^{14}$; CHR$^{17}$R$^{18}$; optionally substituted alkoxycarbonyl; optionally substituted acyl; optionally substituted C$_1$-C$_6$ alkyl; optionally substituted C$_2$-C$_6$ alkenyl; optionally substituted C$_2$-C$_6$ alkynyl; optionally substituted alkoxy; optionally substituted alkoxy C$_1$-C$_6$ alkyl; optionally substituted aminoalkyl; optionally substituted acyl; optionally substituted aryl; optionally substituted C$_1$-C$_6$ alkyl aryl; optionally substituted aryl C$_1$-C$_6$ alkyl; optionally substituted heteroaryl; optionally substituted C$_1$-C$_6$ alkyl heteroaryl; optionally substituted heteroaryl C$_1$-C$_6$ alkyl; optionally substituted C$_2$-C$_6$ alkenyl aryl; optionally substituted aryl C$_2$-C$_6$ alkenyl; optionally substituted C$_2$-C$_6$ alkenyl heteroaryl; optionally substituted heteroaryl C$_2$-C$_6$ alkenyl; optionally substituted C$_3$-C$_8$-cycloalkyl; optionally substituted heterocycloalkyl; optionally substituted C$_1$-C$_6$ alkyl C$_3$-C$_8$-cycloalkyl; optionally substituted C$_3$-C$_8$-cycloalkyl C$_1$-C$_6$ alkyl; optionally substituted C$_1$-C$_6$ alkyl heterocycloalkyl and optionally substituted heterocycloalkyl C$_1$-C$_6$ alkyl; R$^{13}$, R$^{14}$, R$^{17}$ and R$^{18}$ are independently selected from H; optionally substituted C$_1$-C$_6$ alkyl; optionally substituted C$_2$-C$_6$ alkenyl; optionally substituted C$_2$-C$_6$ alkynyl; optionally substituted aryl; optionally substituted C$_1$-C$_6$ alkyl aryl; optionally substituted aryl C$_1$-C$_6$ alkyl; optionally substituted heteroaryl; optionally substituted C$_1$-C$_6$ alkyl heteroaryl; optionally substituted heteroaryl C$_1$-C$_6$ alkyl; optionally substituted C$_2$-C$_6$ alkenyl aryl; optionally substituted aryl C$_2$-C$_6$ alkenyl; optionally substituted C$_2$-C$_6$ alkenyl heteroaryl; optionally substituted heteroaryl C$_2$-C$_6$ alkenyl; optionally substituted C$_3$-C$_8$-cycloalkyl; optionally substituted heterocycloalkyl; optionally substituted C$_1$-C$_6$ alkyl C$_3$-C$_8$-cycloalkyl; optionally substituted C$_3$-C$_8$-cycloalkyl C$_1$-C$_6$ alkyl; optionally substituted C$_1$-C$_6$ alkyl heterocycloalkyl and optionally substituted heterocycloalkyl C$_1$-C$_6$ alkyl; X is NR$^{12}$; Z is selected from C(O); C(S) and SO$_2$; n is 1; and pharmaceutically acceptable salts thereof.

2. The compound according to claim 1 wherein R$^1$ is selected from optionally substituted aryl and optionally substituted heteroaryl.

3. The compound according to claim 1 wherein R$^{12}$ is selected from optionally substituted aryl C$_1$-C$_6$ alkyl and optionally substituted heteroaryl C$_1$-C$_6$ alkyl.

4. The compound according to claim 1 wherein R$^{12}$ is optionally substituted alkoxycarbonyl.

5. The compound according to claim 1 wherein R$^2$, R$^3$, R$^4$, R$^5$, R$^6$, R$^7$, R$^8$, R$^9$, R$^{10}$ and R$^{11}$ are H.

6. The compound according to claim 1 selected from:
2-(2-chlorophenyl)-10-(pyridin-2-ylmethyl)-2,3,8,9,10,11-hexahydro-1H-pyrazolo[4',3':3,4]pyrido[1,2-a][1,4]diazepine-1,5(7H)-dione;
10-benzyl-2-(2-methoxyphenyl)-2,3,8,9,10,11-hexahydro-1H-pyrazolo[4',3':3,4]pyrido[1,2-a][1,4]diazepine-1,5(7H)-dione;
10-benzyl-2-(2-chlorophenyl)-2,3,8,9,10,11-hexahydro-1H-pyrazolo[4',3':3,4]pyrido[1,2-a][1,4]diazepine-1,5(7H)-dione;
10-(2-chlorobenzyl)-2-(2-chlorophenyl)-2,3,8,9,10,11-hexahydro-1H-pyrazolo[4',3':3,4]pyrido[1,2-a][1,4]diazepine-1,5(7H)-dione;
2-(2-chlorophenyl)-10-(3-methoxybenzyl)-2,3,8,9,10,11-hexahydro-1H-pyrazolo[4',3':3,4]pyrido[1,2-a][1,4]diazepine-1,5(7H)-dione;
10-(3-chlorobenzyl)-2-(2-chlorophenyl)-2,3,8,9,10,11-hexahydro-1H-pyrazolo[4',3':3,4]pyrido[1,2-a][1,4]diazepine-1,5(7H)-dione;
2-(2-chlorophenyl)-2,3,8,9,10,11-hexahydro-1H-pyrazolo[4',3':3,4]pyrido[1,2-a][1,4]diazepine-1,5(7H)-dione;
tert-butyl 2-(2-chlorophenyl)-1,5-dioxo-2,3,5,8,9,11-hexahydro-1H-pyrazolo[4',3':3,4]pyrido[1,2-a][1,4]diazepine-10(7H)-carboxylate;
10-(4-chlorobenzyl)-2-(2-chlorophenyl)-2,3,8,9,10,11-hexahydro-1H-pyrazolo[4',3':3,4]pyrido[1,2-a][1,4]diazepine-1,5(7H)-dione;
2-(2-chlorophenyl)-10-(2-methoxybenzyl)-2,3,8,9,10,11-hexahydro-1H-pyrazolo[4',3':3,4]pyrido[1,2-a][1,4]diazepine-1,5(7H)-dione;
2-(2-chlorophenyl)-10-(4-methoxybenzyl)-2,3,8,9,10,11-hexahydro-1H-pyrazolo[4',3':3,4]pyrido[1,2-a][1,4]diazepine-1,5(7H)-dione;
2-(2-chlorophenyl)-10-(furan-3-ylmethyl)-2,3,8,9,10,11-hexahydro-1H-pyrazolo[4',3':3,4]pyrido[1,2-a][1,4]diazepine-1,5(7H)-dione;
2-(2-methoxyphenyl)-10-(pyridin-2-ylmethyl)-2,3,8,9,10,11-hexahydro-1H-pyrazolo[4',3': 3,4]pyrido[1,2-a][1,4]diazepine-1,5(7H)-dione;
10-(3-methoxybenzyl)-2-(2-methoxyphenyl)-2,3,8,9,10,11-hexahydro-1H-pyrazolo[4',3':3,4]pyrido[1,2-a][1,4]diazepine-1,5(7H)-dione;
2-(2-chlorophenyl)-10-[(1-methyl-1H-pyrazol-3-yl)methyl]-2,3,8,9,10,11-hexahydro-1H-pyrazolo[4',3':3,4]pyrido[1,2-a][1,4]diazepine-1,5(7H)-dione; or
2-(2-chlorophenyl)-10-(pyridin-3-ylmethyl)-2,3,8,9,10,11-hexahydro-1H-pyrazolo[4',3':3,4]pyrido[1,2-a][1,4]diazepine-1,5(7H)-dione.

7. A pharmaceutical composition containing at least one compound according to claim 1 and a pharmaceutically acceptable carrier, diluent or excipient.

8. A method for treating a patient suffering from a disease or condition selected from pulmonary hypertension, chronic obstructive pulmonary diseases (COPD), hypertension, atherosclerosis, pulmonary fibrosis, Alzheimer's disease, diabetes, asthma, hearing loss, balance problems in response to ototoxic drugs, vascular injury after balloon, surgery, inflammation, cardiovascular complications of Type I or Type II diabetes, intimal hyperplasia, coronary heart disease, cerebral, coronary or arterial vasospasm, endothelial dysfunction, inflammatory bowel disease, Crohn's disease, multiple sclerosis, pain, diabetic nephropathy, liver fibrosis, alcohol induced fibrosis, steatosis or non-alcoholic steatohepatitis, fibrosarcoma, myxosarcoma, liposarcoma, chondrosarcoma, osteogenic sarcoma, chordoma, angiosarcoma, endothelium sarcoma, lymphangiosarcoma, lymphangioendothelioma, periosteoma, mesothelioma, Ewing's tumor, leiomyosarcoma, rhabdomyosarcoma, colon carcinoma, pancreatic cancer, breast cancer, ovarian cancer, renal cancer, prostatic carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, embryonal carcinoma, Wilms' tumor, cervical cancer, orchioncus, lung cancer, small-cell lung cancer, lung adenocarcinoma, bladder cancer and epithelial cancer, the method comprising administering a pyrazoline dione compound or a pharmaceutically active salt thereof according to claim 1 to a patient having said disease or condition.

9. A process for the preparation of a pyrazoline dione compound according to Formula (I), comprising the step of cyclizing a compound of Formula (II) in presence of a base:

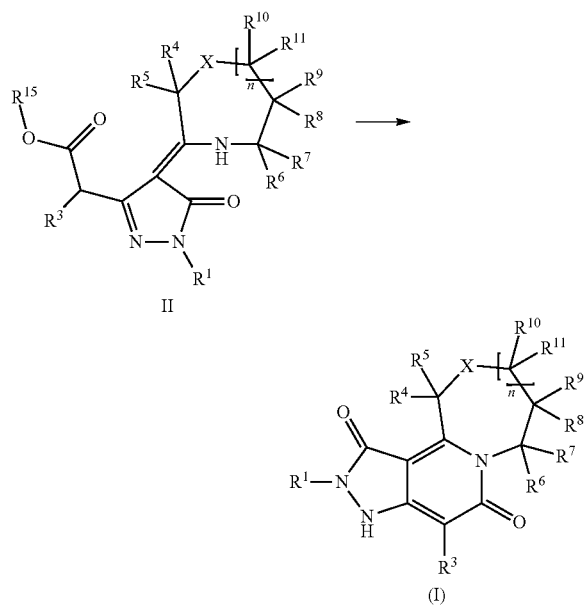

wherein $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, X and n are as defined in claim 1, and $R^{15}$ is an optionally substituted $C_1$-$C_6$ alkyl and $R^2$ is H.

10. A process for the preparation of a pyrazoline dione compound according to Formula (I), comprising reacting a compound of Formula (Ia) with an alkylating agent or a coupling agent in presence of a base:

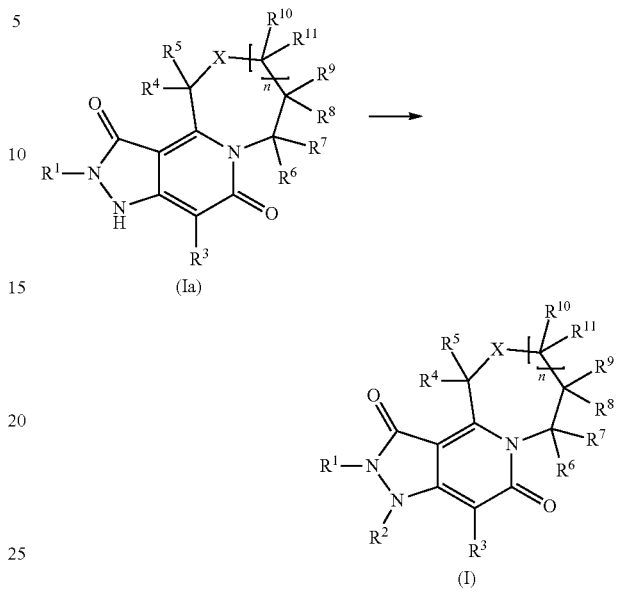

wherein $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{17}$, $R^{18}$, X and n are as defined in claim 1 and $R^2$ is optionally substituted alkoxycarbonyl; optionally substituted acyl; optionally substituted acyl $C_1$-$C_6$ alkyl; optionally substituted $C_1$-$C_6$ alkyl; optionally substituted $C_2$-$C_6$ alkenyl; optionally substituted $C_2$-$C_6$ alkynyl; optionally substituted aryl; optionally substituted heteroaryl; optionally substituted $C_3$-$C_8$-cycloalkyl; optionally substituted heterocycloalkyl; optionally substituted $C_3$-$C_8$-cycloalkyl $C_1$-$C_6$ alkyl; optionally substituted heterocycloalkyl $C_1$-$C_6$ alkyl; optionally substituted aryl $C_1$-$C_6$ alkyl or optionally substituted heteroaryl $C_1$-$C_6$ alkyl.

11. A method for inhibiting angiogenesis in a patient comprising administering an angiogenesis inhibiting dose of a pyrazoline dione compound according to claim 1, or a pharmaceutically active salt thereof to said patient.

12. The compound according to claim 1, wherein X is $NR^{12}$.

13. The compound according to claim 1, wherein X is NH.

14. The method according to claim 8, wherein said disease or condition is cancer selected from fibrosarcoma, myxosarcoma, liposarcoma, chondrosarcoma, osteogenic sarcoma, chordoma, angiosarcoma, endothelium sarcoma, lymphangiosarcoma, lymphangioendothelioma, periosteoma, mesothelioma, Ewing's tumor, leiomyosarcoma, rhabdomyosarcoma, colon carcinoma, pancreatic cancer, breast cancer, ovarian cancer, renal cancer, prostatic carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, lung embryonal carcinoma, Wilms' tumor, cervical cancer, orchioncus, lung cancer, small-cell lung cancer, lung adenocarcinoma, bladder cancer and epithelial cancer.

15. The method according to claim 8, wherein said disease or condition is selected from pulmonary hypertension, chronic obstructive pulmonary diseases (COPD), hypertension, atherosclerosis, pulmonary fibrosis, Alzheimer's disease, diabetes, asthma, hearing loss, balance problems in response to ototoxic drugs, vascular injury after balloon surgery, inflammation, cardiovascular complications of Type I or Type II diabetes, intimal hyperplasia, coronary heart disease, cerebral, coronary or arterial vasospasm, endothelial dysfunction, inflammatory bowel disease, Crohn's disease, multiple sclerosis, pain, diabetic nephropathy, liver fibrosis, alcohol induced fibrosis, and steatosis or non-alcoholic steatohepatitis.

16. The method according to claim 8, wherein said disease or condition is hypertension.

17. The method according to claim 8, wherein said disease or condition is atherosclerosis.

18. The method according to claim 8, wherein said disease or condition is pulmonary fibrosis.

19. The method according to claim 8, wherein said disease or condition is pulmonary hypertension.

20. The method according to claim 8, wherein said disease or condition is chronic obstructive pulmonary disease (COPD).

21. The method according to claim 8, wherein said disease or condition is diabetes.

22. The method according to claim 8, wherein said disease or condition is cardiovascular complications of Type I or Type II diabetes.

* * * * *